(12) United States Patent
Burdge

(10) Patent No.: US 10,668,265 B2
(45) Date of Patent: Jun. 2, 2020

(54) SINGLE-USE ASEPTIC FLUID COUPLINGS

(71) Applicant: Colder Products Company, St. Paul, MN (US)

(72) Inventor: David Alan Burdge, Richfield, MN (US)

(73) Assignee: Colder Products Company, St. Paul, MN (US)

( * ) Notice: Subject to any disclaimer, the term of this patent is extended or adjusted under 35 U.S.C. 154(b) by 0 days.

(21) Appl. No.: 16/013,501

(22) Filed: Jun. 20, 2018

(65) Prior Publication Data

US 2018/0296817 A1     Oct. 18, 2018

Related U.S. Application Data

(63) Continuation of application No. 15/133,950, filed on Apr. 20, 2016, now Pat. No. 10,022,532.

(60) Provisional application No. 62/150,087, filed on Apr. 20, 2015.

(51) Int. Cl.
| | | |
|---|---|---|
| *A61M 39/10* | (2006.01) | |
| *F16L 37/35* | (2006.01) | |
| *A61M 39/26* | (2006.01) | |

(52) U.S. Cl.
CPC ........ *A61M 39/1011* (2013.01); *A61M 39/26* (2013.01); *F16L 37/35* (2013.01); *A61M 2039/1033* (2013.01); *F16L 2201/20* (2013.01); *F16L 2201/44* (2013.01)

(58) Field of Classification Search
USPC ......................................... 137/798; 251/89.5
See application file for complete search history.

(56) References Cited

U.S. PATENT DOCUMENTS

| | | |
|---|---|---|
| 4,334,551 A | 6/1982 | Pfister |
| 4,429,713 A | 2/1984 | Walter |
| 4,664,148 A | 5/1987 | Magnuson |
| 4,804,015 A | 2/1989 | Albinsson |
| 5,806,564 A | 9/1998 | Wilcox |
| 5,971,019 A | 10/1999 | Imal |
| 6,161,578 A | 12/2000 | Braun et al. |
| 6,237,631 B1 | 5/2001 | Giesler et al. |
| 7,469,472 B2 | 12/2008 | deCler et al. |
| 7,547,047 B2 | 6/2009 | deCler et al. |
| 7,959,192 B2 | 6/2011 | Elton et al. |
| 8,690,120 B2 | 4/2014 | Hartnett et al. |
| 2007/0073215 A1 | 3/2007 | Wieslander |
| 2008/0185056 A1 | 8/2008 | Diodati et al. |
| 2009/0051161 A1 | 2/2009 | Eskstrom |

(Continued)

FOREIGN PATENT DOCUMENTS

| | | |
|---|---|---|
| EP | 0028601 | 5/1981 |
| WO | WO 1980/001507 | 7/1980 |

(Continued)

OTHER PUBLICATIONS

European Extended Search Report in European Application No. EP16854486, dated May 20, 2019, 7 pages.

(Continued)

*Primary Examiner* — Jessica Cahill
*Assistant Examiner* — Daphne M Barry
(74) *Attorney, Agent, or Firm* — Fish & Richardson P.C.

(57) ABSTRACT

Some fluid coupling devices described herein are configured for use in fluid systems for purposes of providing a single-use, aseptic disconnection functionality that substantially prevents fluid spillage when being disconnected.

12 Claims, 18 Drawing Sheets

(56) References Cited

U.S. PATENT DOCUMENTS

| | | |
|---|---|---|
| 2009/0076434 A1 | 3/2009 | Mischelevich |
| 2010/0230950 A1 | 9/2010 | Scott et al. |
| 2011/0240158 A1 | 10/2011 | Py |
| 2012/0031515 A1 | 2/2012 | Whitaker |
| 2013/0341904 A1 | 12/2013 | Lehmann et al. |
| 2014/0345748 A1 | 11/2014 | Rogers et al. |
| 2016/0158519 A1 | 6/2016 | Rhinehart |
| 2019/0298985 A1 | 10/2019 | Truong |

FOREIGN PATENT DOCUMENTS

| | | |
|---|---|---|
| WO | WO 2008/094707 | 8/2008 |
| WO | WO 2012/114105 | 8/2012 |
| WO | WO 2014/160756 | 10/2014 |
| WO | WO 2017/062859 | 4/2017 |

OTHER PUBLICATIONS

International Preliminary Report on Patentability in International Application No. PCT/US2016/028467, dated Oct. 24, 2017 9 pages.
International Search Report and Written Opinion in International Application No. PCT/US2016/028467, dated Jul. 26, 2016, 9 pages.
International Search Report and Written Opinion in International Application No. PCT/US2016/056120, dated Dec. 13, 2016, 18 pages.
International Preliminary Report on Patentability in International Application No. PCT/US2016/056120, dated Apr. 10, 2018, 11 pages.
European Extended Search Report in European Application No. EP16783779, dated Oct. 31, 2018, 9 pages.

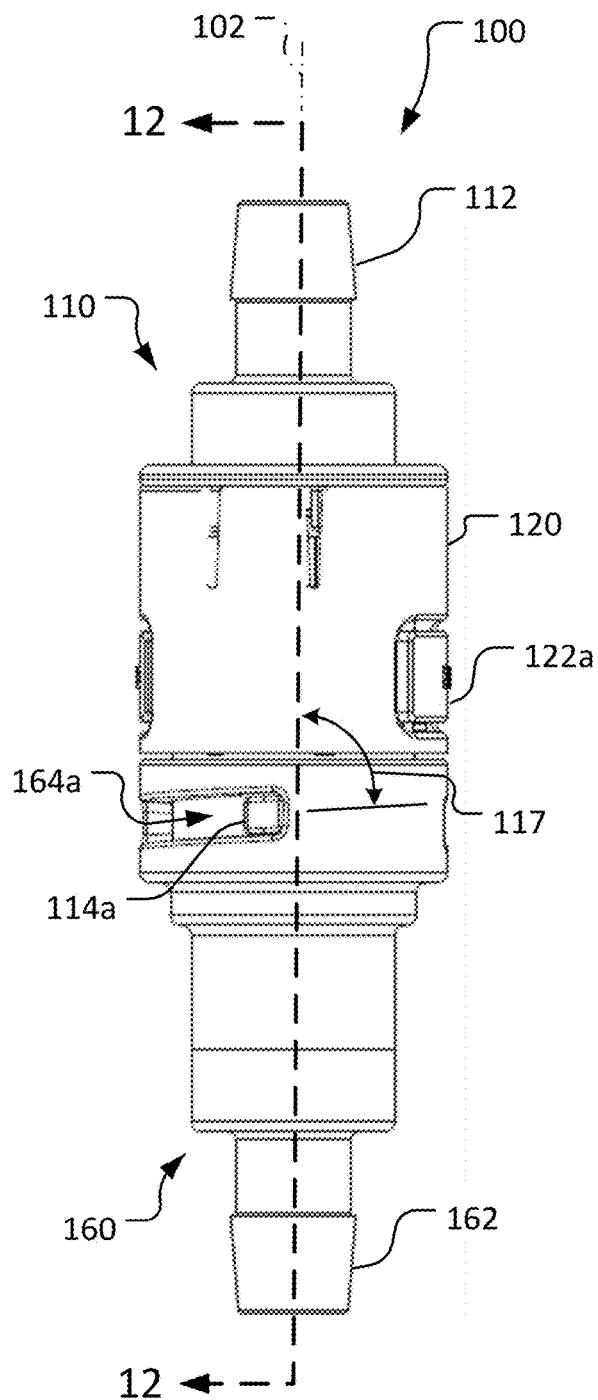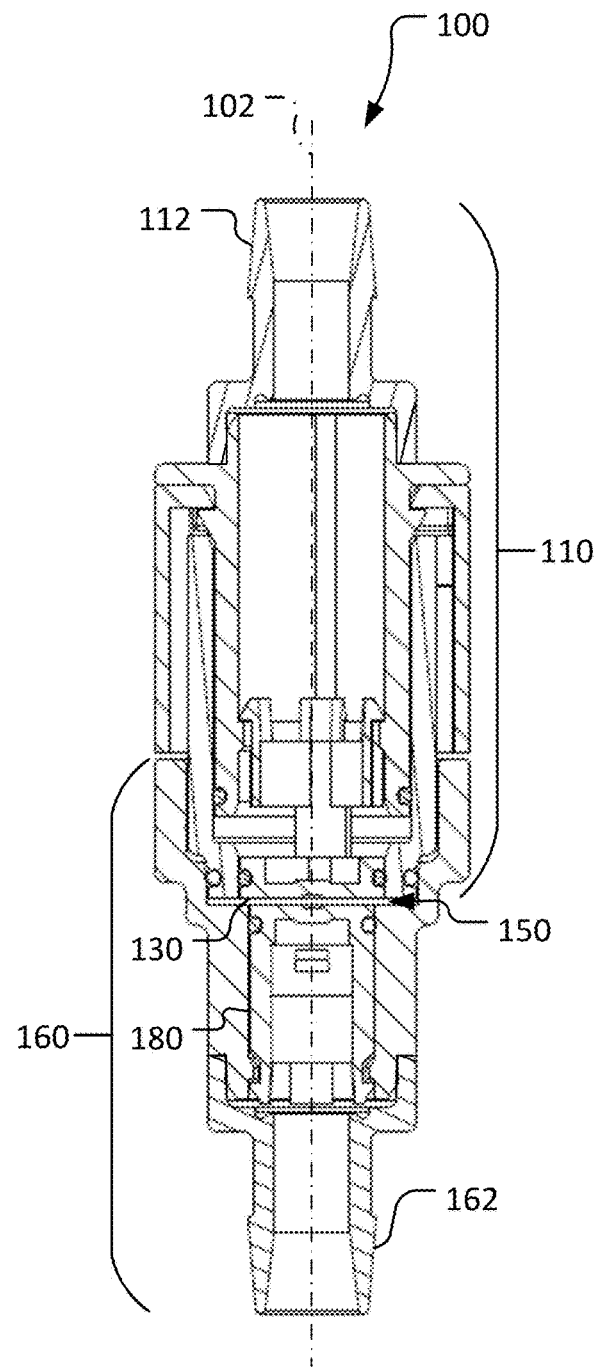
FIG. 11  FIG. 12

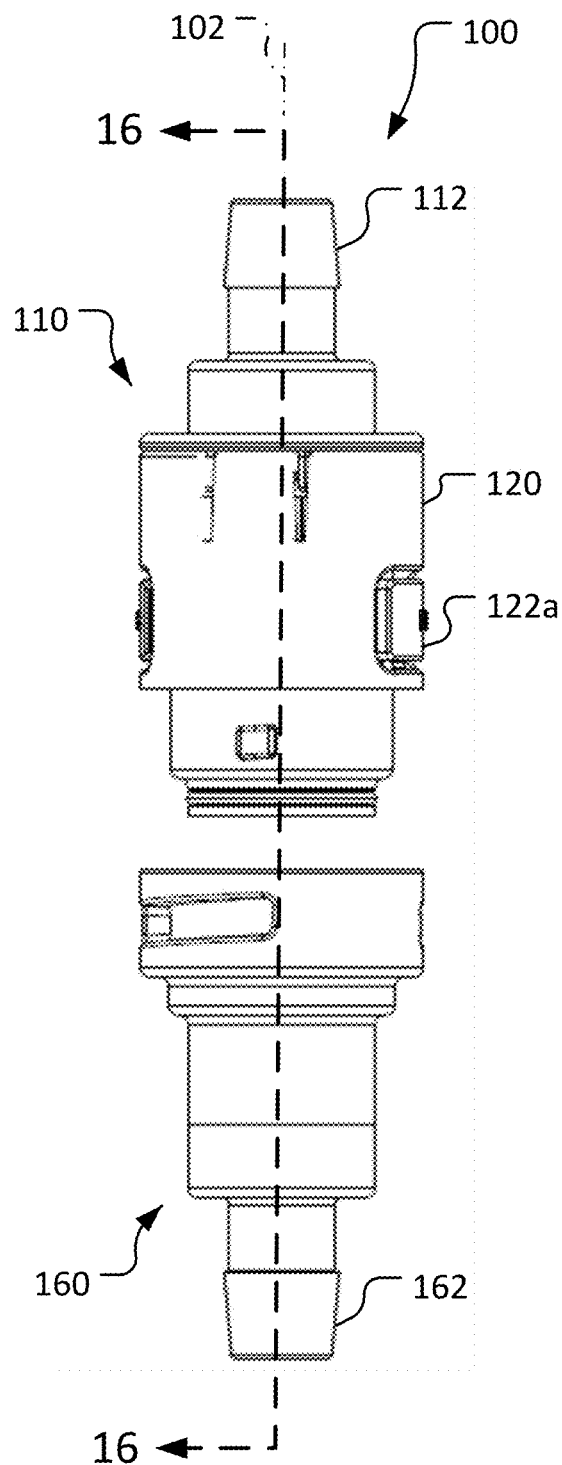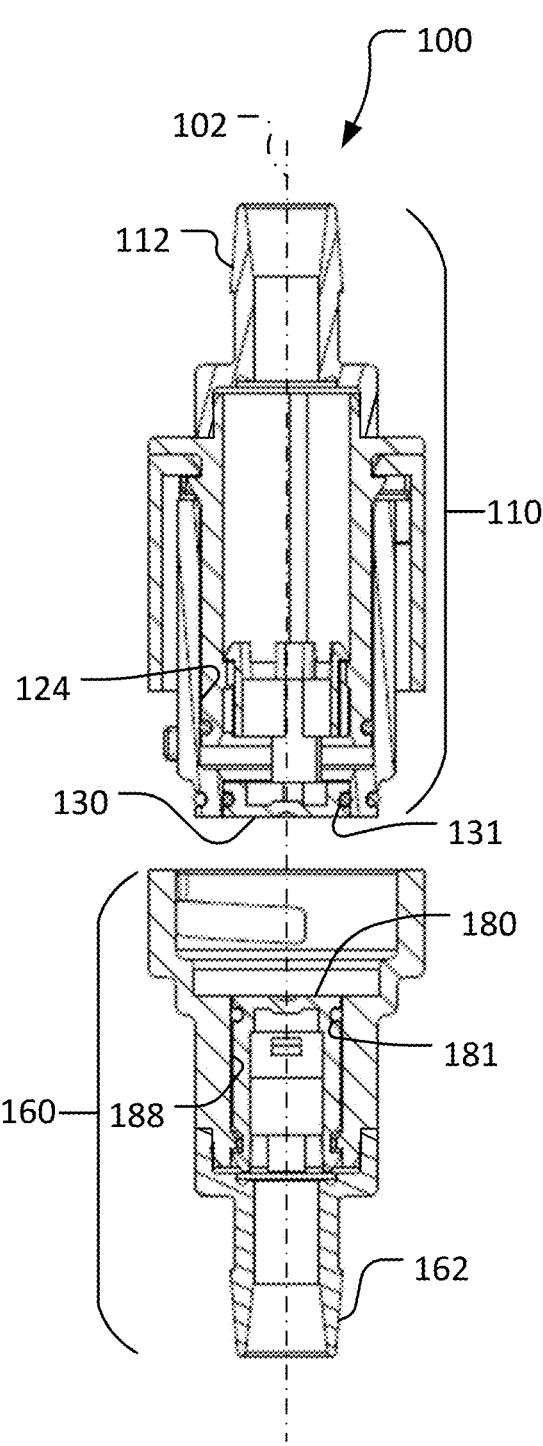
FIG. 15  FIG. 16

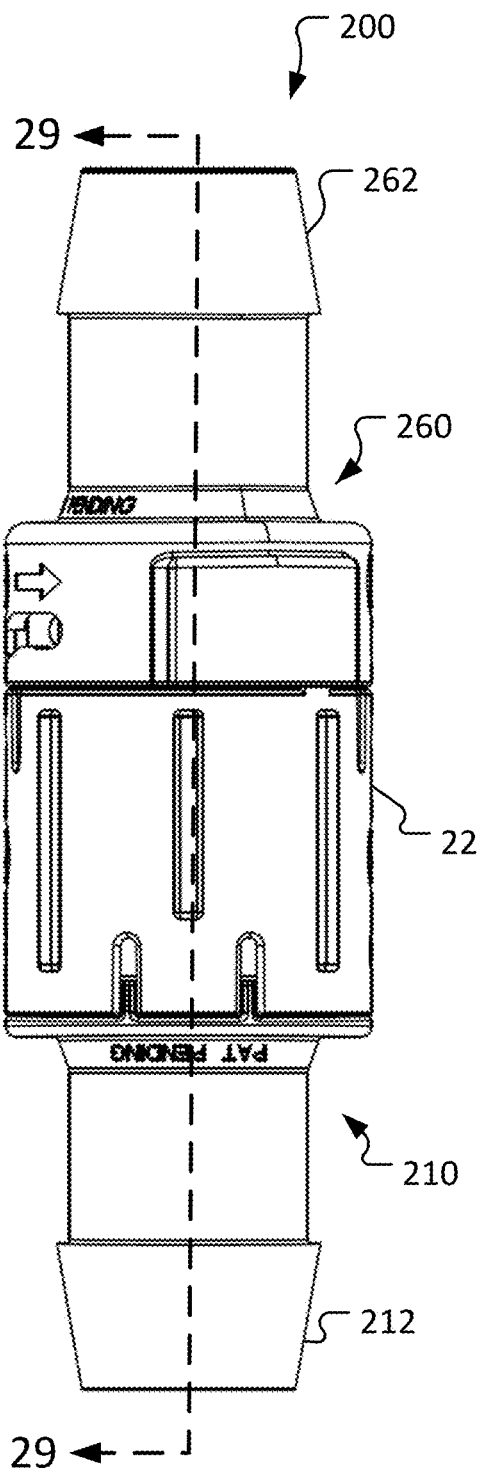
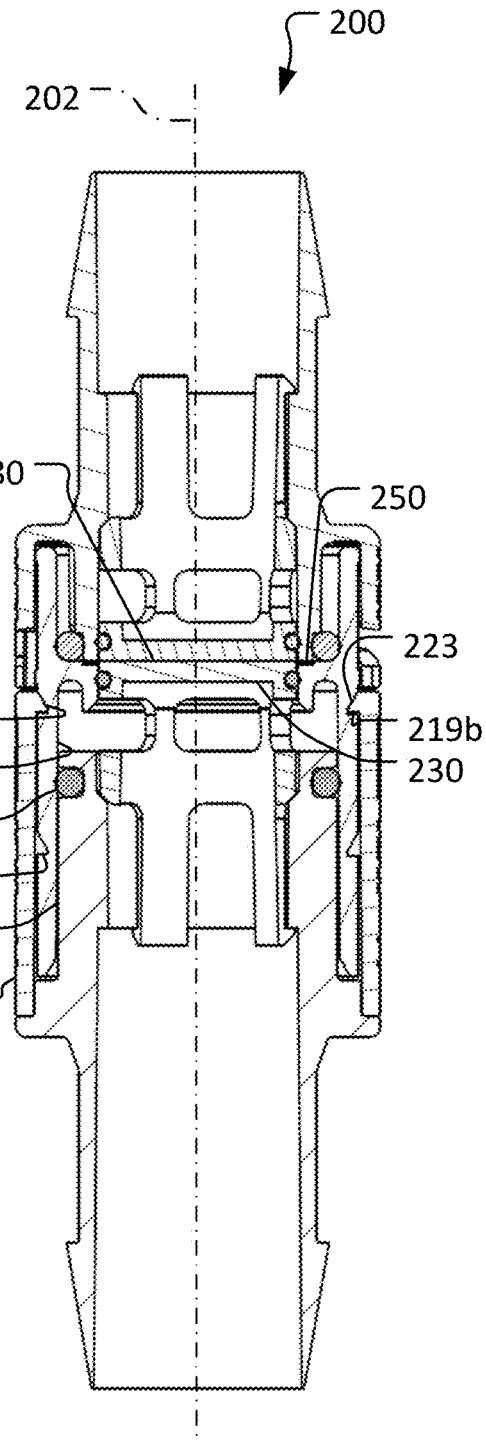
FIG. 28  FIG. 29

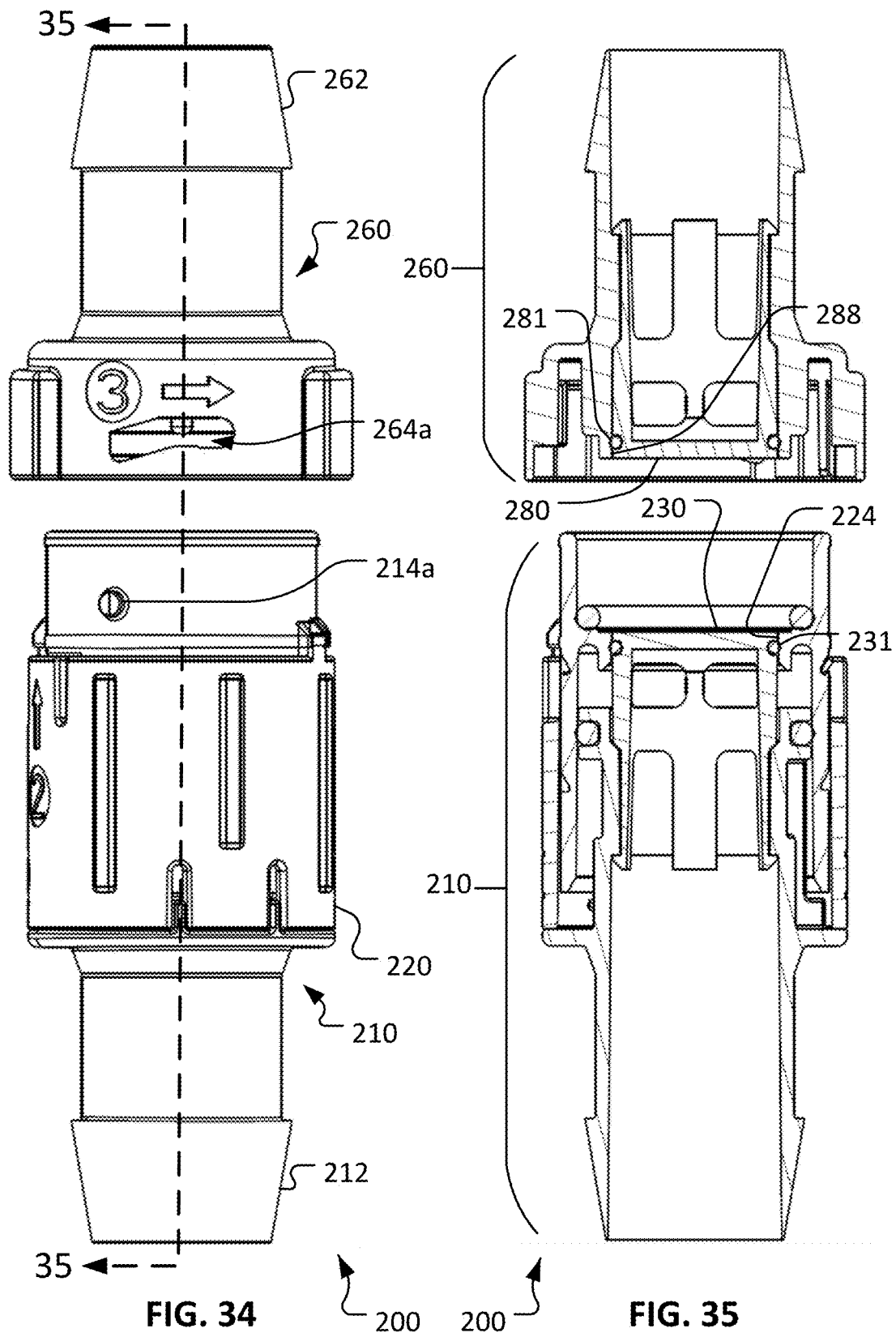

SINGLE-USE ASEPTIC FLUID COUPLINGS

CROSS-REFERENCE TO RELATED APPLICATIONS

This application is a continuation of U.S. application Ser. No. 15/133,950, filed Apr. 20, 2016, which claims the benefit of U.S. Provisional Application Ser. No. 62/150,087, filed Apr. 20, 2015. The disclosure of the prior application is considered part of (and is incorporated by reference in) the disclosure of this application.

BACKGROUND

1. Technical Field

This document relates to fluid coupling devices for fluid systems and methods. For example, some embodiments described in this document relate to single-use, aseptic disconnection fluid coupling devices.

2. Background Information

Fluid systems commonly include components such as tubing, pumps, reservoirs, fittings, couplings, heat exchangers, sensors, filters, valves, seals, and the like. Such components can be connected together in a network to define one or more fluid flow paths. Some fluid systems are open systems, meaning that the fluid flows through the network once and then exits the network. Other fluid systems are closed systems, meaning that the fluid recirculates within the network of components. Fluids may be moved through fluid systems using fluid pressure differentials. For example, in some cases, a pump or a vacuum source is used to create a pressure differential that causes the fluid to flow within the fluid system. In another example, gravity is used to cause the fluid to flow within the fluid system. In other examples, a combination of such techniques is used to cause the fluid to flow within the fluid system.

In the context of some fluid systems, such as some bioprocessing fluid systems, it may be desirable to have a coupler that can aseptically disconnect a fluid flow path. In one such example implementation, it is desirable to aseptically disconnect one or more media bags from a bioreactor system. In that scenario, an aseptic coupling can be used to disconnect the media bag(s) from the bioreactor system while substantially preventing biological contamination of the media bags and of the bioreactor via the disconnected ends of the coupling during and after the disconnection process. Such an aseptic coupling will also serve to limit the exposure of the fluid to the surrounding environment.

SUMMARY

This document describes a number of fluid coupling devices for fluid systems and methods. In some embodiments, the fluid coupling devices can be implemented as single-use, aseptic disconnection fluid coupling devices that are configured to reduce the likelihood of fluid spillage when being disconnected. In the context of this disclosure, the term "fluid" includes both gases and liquids.

In particular embodiments, the fluid coupling devices described herein are single-use devices because, after the two portions of the coupling (also referred to herein as "coupling halves" and/or "connectors") are disconnected from each other, the fluid paths of both portions are irreversibly blocked. For example, such single-use coupling devices are equipped with one or more mechanical components that operates such that, even if the coupling halves are reconnected to each other after being disconnected, the flow paths will remain blocked. Hence, in these particular embodiments, the fluid coupling devices provided herein are structurally configured to be single-use disconnection devices so that, after the single-use coupling halves have been disconnected from each other, they cannot be operably reconnected to each other (or to any other coupling halves).

Additionally, in such single-use embodiments or in other embodiments, the fluid coupling devices can be configured as "aseptic" coupling devices in that, after the two portions of the coupling device are disconnected from each other, the fluid paths of both portions are mechanically blocked so as to inhibit biological contamination migrating into the flow paths. Such an "aseptic" coupling will also serve to limit the exposure of the fluid to the surrounding environment.

Further, in such single-use embodiments, or other embodiments, the fluid coupling devices can be configured as no-spill coupling devices because, as the two portions of the coupling device are being disconnected from each other, one or more mechanical components will reduce the likelihood of fluid discharge out of the fluid system (for example, by blocking as such discharge paths).

In one implementation, a fluid coupling device includes a male connector component. The male connector component defines a first male connector internal space and a second male connector internal space. The fluid coupling device also includes a male coupling shuttle valve member partially disposed within the first male connector internal space and partially disposed within the second male connector internal space. The fluid coupling device also includes a locking sleeve coupled to the male connector component. The fluid coupling device also includes a female connector component that is releasably matable with the male connector component. The female connector component defines a female connector internal space. The fluid coupling device also includes a female coupling shuttle valve member at least partially disposed within the female connector internal space. The female coupling shuttle valve member is also partially disposed within the second male connector internal space when the female connector component releasably mates with the male connector component.

Such a fluid coupling device may also include one or more of the following optional features. In some embodiments, a cross-sectional shape of each of the male coupling shuttle valve member and the female coupling shuttle valve member is non-circular. The locking sleeve may be coupled with the male coupling shuttle valve member. In various embodiments, the male coupling shuttle valve member and the female coupling shuttle valve member are each the same physical shape. The locking sleeve may be slidably coupled to the male connector component. In some embodiments, the locking sleeve comprises one or more unlocking members that must be actuated prior to sliding the locking sleeve in relation to the male connector component. The male coupling shuttle valve member and the female coupling shuttle valve member may each include one or more apertures. In some embodiments, all elements of the fluid coupling device are non-metallic. In particular embodiment, when the male connector component is fully disconnected from the female connector component, the male coupling shuttle valve member blocks fluid flow through the first male connector internal space and blocks fluid flow through the second male connector internal space, and the female coupling shuttle valve member blocks fluid flow through the female connector internal space. Optionally, the male connector component and the female connector component are releasably coupled via a bayonet connection.

In another implementation, a fluid coupling device includes a male connector component and a male coupling shuttle valve member disposed within the male connector component. The fluid coupling device also includes a locking sleeve coupled to the male connector component. The locking sleeve is coupled to the male coupling shuttle valve member. The fluid coupling device also includes a female connector component releasably matable to the male connector component, and a female coupling shuttle valve member partially disposed within the male connector component and partially disposed within the female connector component when the female connector component releasably mates with the male connector component.

Such a fluid coupling device may optionally include one or more of the following features. The locking sleeve may be slidably coupled to the male connector component. In some embodiments, sliding the locking sleeve longitudinally along the male connector component also longitudinally slides the male coupling shuttle valve member and the female coupling shuttle valve member within the fluid coupling device. In particular embodiments, the sliding the locking sleeve may cause a blockage of fluid flow through the fluid coupling device. The blockage of the fluid flow through the fluid coupling device may be irreversible in some implementations. Optionally, no components other than seals are under substantial mechanical stress while the female connector component releasably mates with the male connector component. In some embodiments, the fluid coupling device is metallic-free. The fluid coupling device may define a fluid flow path through the fluid coupling device. The fluid flow path may extend through: a) a first male connector internal space defined by the male connector component, b) an internal male coupling shuttle valve member space defined by the male coupling shuttle valve member, c) a second male connector internal space defined by the male connector component, d) an internal female coupling shuttle valve member space defined by the female coupling shuttle valve member, and e) a female connector internal space defined by the female connector component. In some embodiments, the sliding the locking sleeve along the male connector component toward the female connector component causes a blockage of the fluid flow path. In particular embodiments, the blockage of the fluid flow path is irreversible.

In another implementation, a fluid system is provided that includes a first fluid system equipment or container, a second fluid system equipment or container, and a single-use, aseptic disconnection fluid coupling device. The single-use, aseptic disconnection fluid coupling device is configured to provide a fluid path between the first fluid system equipment or container and the second fluid system equipment or container. The single-use, aseptic disconnection fluid coupling device includes a male connector component releasably lockable with a corresponding female connector component, a male coupling shuttle valve member disposed within the male connector component, and a locking sleeve coupled to the male connector component. The locking sleeve is coupled to the male coupling shuttle valve member. The single-use, aseptic disconnection fluid coupling device also includes a female coupling shuttle valve member at least partially disposed within the female connector component and partially disposed within the male connector component when the male connector component releasably locks with the female connector component.

In another implementation, a method of using a single-use, aseptic disconnection fluid coupling device includes providing a fluid path through a single-use, aseptic disconnection fluid coupling device and between a first fluid system equipment or container and a second fluid system equipment or container. The method of using a single-use, aseptic disconnection fluid coupling device also includes disconnecting a male connector component of the single-use, aseptic disconnection fluid coupling device from a corresponding female connector component so that the fluid path through each of the male connector component and female connector component are irreversibly and mechanically blocked by a corresponding mechanical element.

Particular embodiments of the subject matter described in this document can be implemented to realize one or more of the following advantages. First, in some embodiments the fluid coupling devices provided herein are configured to allow fluid flow therethrough with a minimized amount of pressure drop. For example, some embodiments of the fluid coupling device can be configured for connection to ½-inch inside diameter tubing while also having a pressure drop that is similar to the pressure drop of an equivalent length of ½-inch inside diameter tubing.

Second, in some embodiments, the fluid coupling devices may advantageously provide a user with audible and/or tactile feedback in reference to the motions performed for physically disconnecting the two portions of the fluid coupling devices from each other. Such audible and/or tactile feedback can provide the user with an efficient and conclusive indication or confirmation of the proper function and desired configuration of the fluid coupling device.

Third, some embodiments of the fluid coupling devices provided herein are a metallic-free construction (also referred to as a nonmetallic fluid coupling device). As such, such embodiments of the nonmetallic fluid coupling devices can be advantageously sterilized using a gamma sterilization technique. Also, in some circumstances, the nonmetallic fluid coupling devices exhibit enhanced fatigue-resistance characteristics, minimal installed stress, and enhanced corrosion resistance in comparison to some fluid couplings that include traditional metallic parts such as metal springs.

Fourth, some embodiments of the fluid coupling devices provide an improved aseptic disconnection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the disconnection of particular fluid couplings in a sterile room or within a sterile flow-hood to prevent biological contamination.

Fifth, some embodiments of the fluid coupling devices provided herein are advantageously designed with a robust locking system. That is, when the two halves of the coupling are operably connected with each other, they are also mechanically locked together. In some embodiments, to release the lock, two buttons on the coupling must be simultaneously depressed. This redundant requirement (e.g., simultaneous actuation of two buttons or other actuators) for unlocking the coupling halves may reduce the likelihood of unintentional disconnections.

Sixth, in some optional embodiments, when the two halves of the fluid coupling devices are mated together, most components of the coupling device are not under substantial mechanical stress that would induce warping. This configuration is advantageous because, for example, the heat associated with some sterilization processes may cause stressed components to warp or to induce warping of other components. Since most of the components of the coupling device are not under substantial mechanical stress during sterilization, the propensity for the coupling device to warp is reduced or substantially eliminated.

Seventh, in some embodiments, the coupling halves of the fluid coupling devices provided herein are coupled via a bayonet connection that is configured to assist with disconnection of the coupling halves. As explained further below, the bayonet connection mechanism includes a non-orthogonal slot that induces a slight longitudinal separation of the coupling halves as the coupling halves are rotated in relation to each other during disconnection. The resulting slight separation is advantageous for breaking a seal (or vacuum) that may exist between the coupling halves, and that may otherwise be difficult or inconvenient for a user to break.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 11 is a first side view of the fluid coupling device of FIG. 3 with the coupling halves of the coupling device positioned in a longitudinally compressed and rotated arrangement (e.g., during the process of disconnecting the coupling halves from each other).

FIG. 12 is a longitudinal cross-sectional view of the fluid coupling device of FIG. 11.

FIG. 15 is a first side view of the fluid coupling device of FIG. 3 with the coupling halves of the coupling device disconnected from each other.

FIG. 16 is a longitudinal cross-sectional view of the fluid coupling device of FIG. 15.

FIG. 28 is a second side view of the fluid coupling device of FIG. 26. The perspective of the second side view of FIG. 28 is about 90° from the first side view of FIG. 26.

FIG. 29 is a longitudinal cross-sectional view of the fluid coupling device of FIG. 28.

FIG. 34 is a side view of the fluid coupling device of FIG. 22 with the coupling halves of the coupling device disconnected from each other.

FIG. 35 is a longitudinal cross-sectional view of the fluid coupling device of FIG. 34.

Like reference numbers represent corresponding parts throughout.

DETAILED DESCRIPTION OF ILLUSTRATIVE EMBODIMENTS

Figure 1:
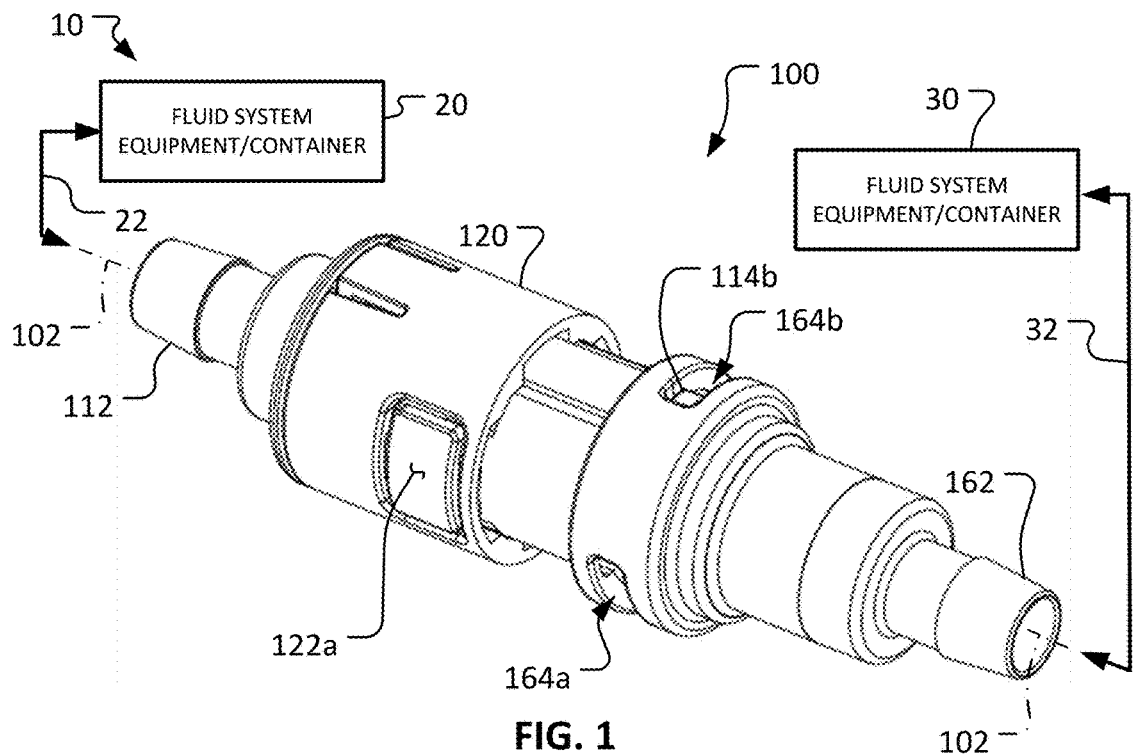
FIG. 1 is a perspective view of an example fluid system including an example fluid coupling device arranged in a connected configuration, in accordance with some embodiments provided herein.
Figure 2:
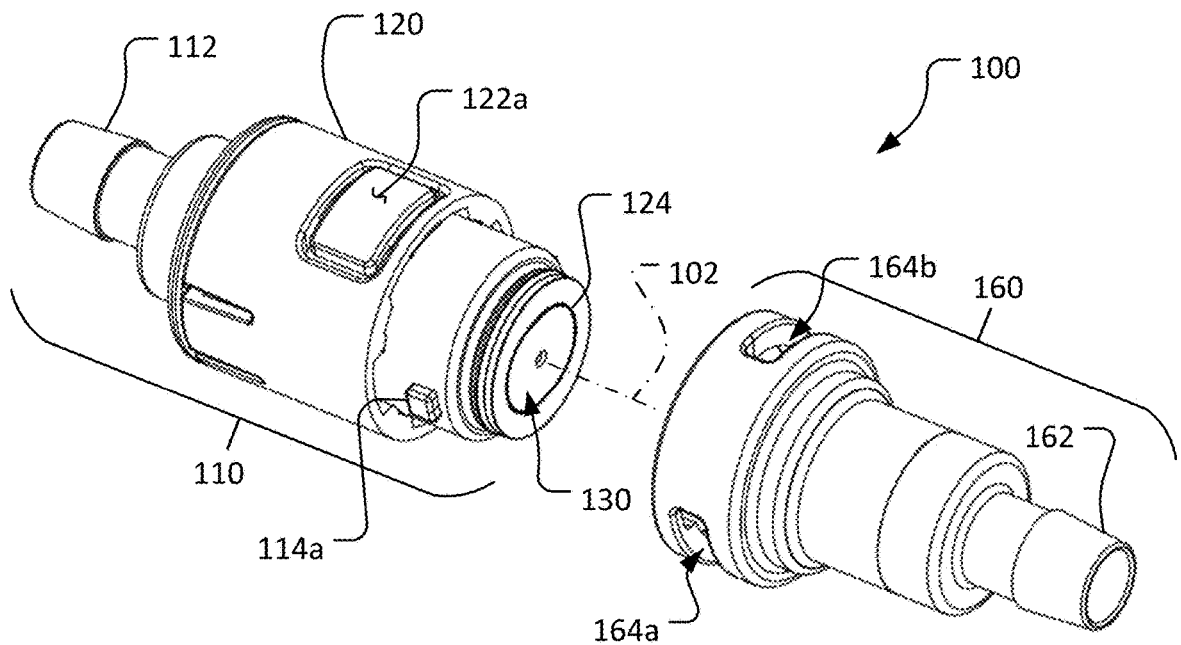
FIG. 2 is a perspective view of the fluid coupling device of FIG. 1 arranged in a disconnected configuration.
Figure 3:
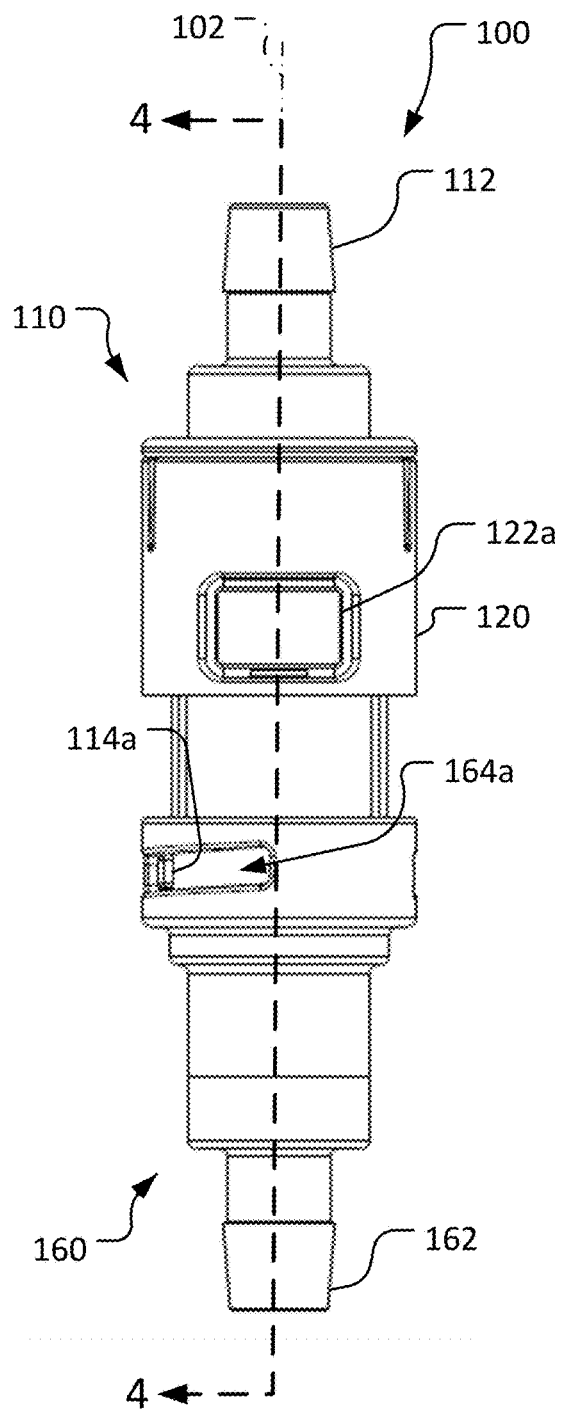
FIG. 3 is a first side view of the fluid coupling device of FIG. 1 with two coupling halves of the coupling device being arranged in a connected and operable configuration.
Figure 4:
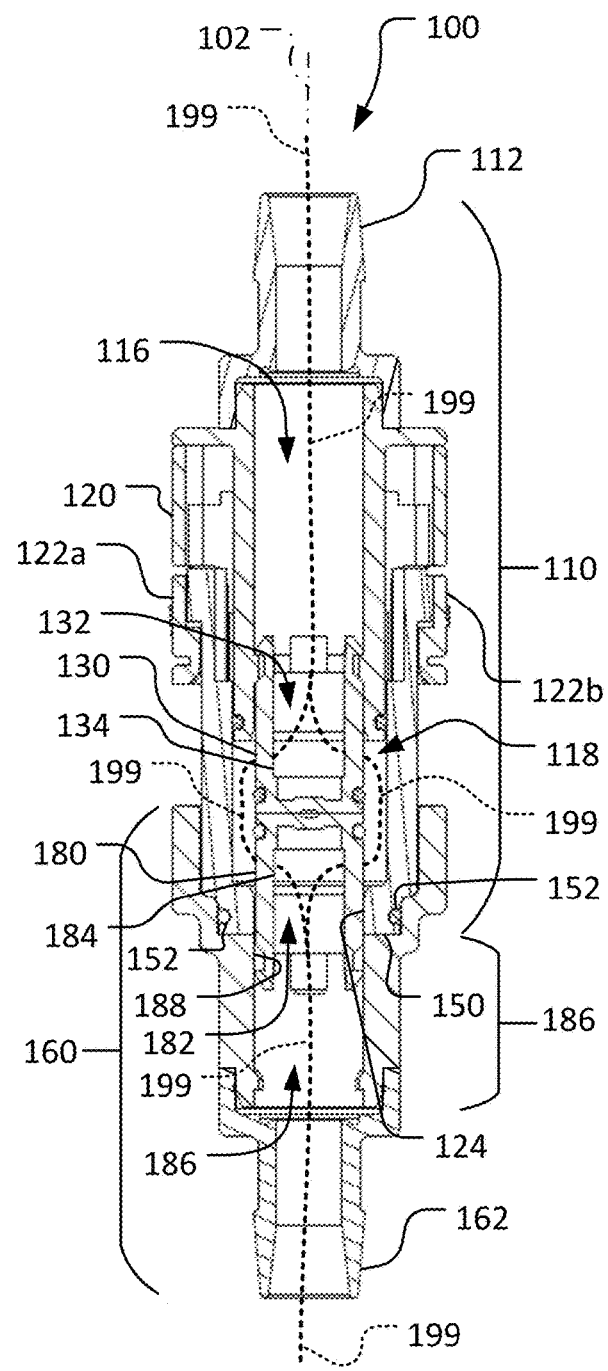
FIG. 4 is a longitudinal cross-sectional view of the fluid coupling device of FIG. 3.
Figure 5:
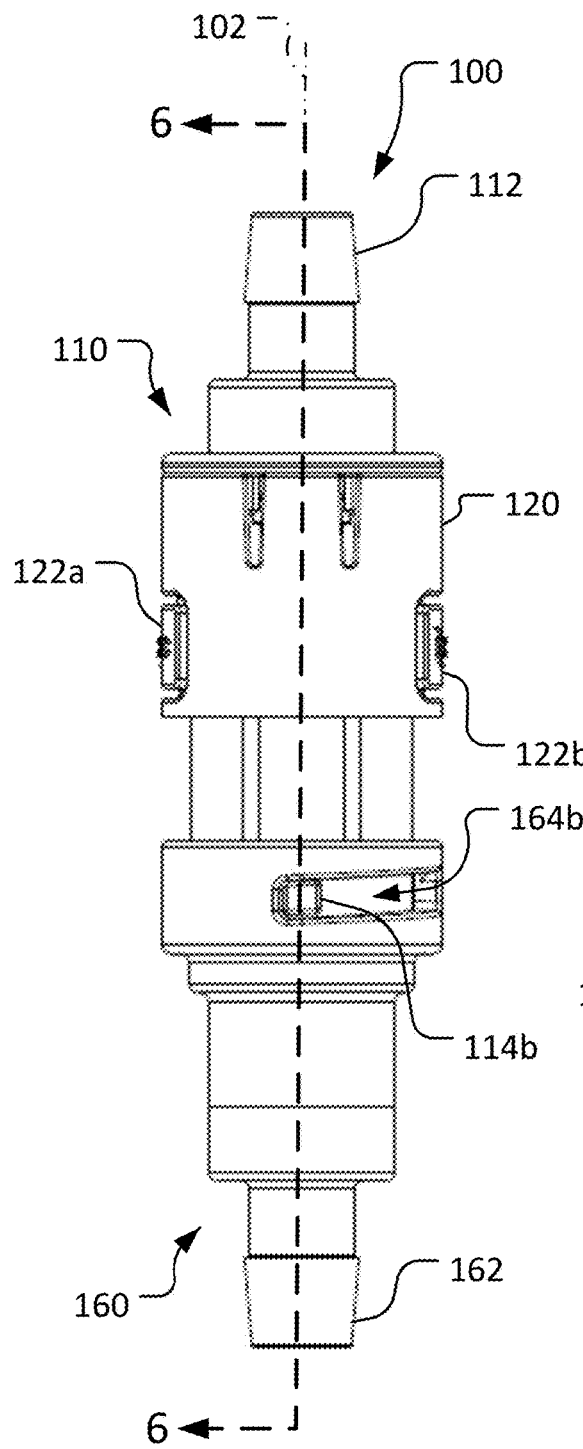
FIG. 5 is a second side view of the fluid coupling device of FIG. 3. The perspective of the second side view of FIG. 5 is 90° from the first side view of FIG. 3.
Figure 6:
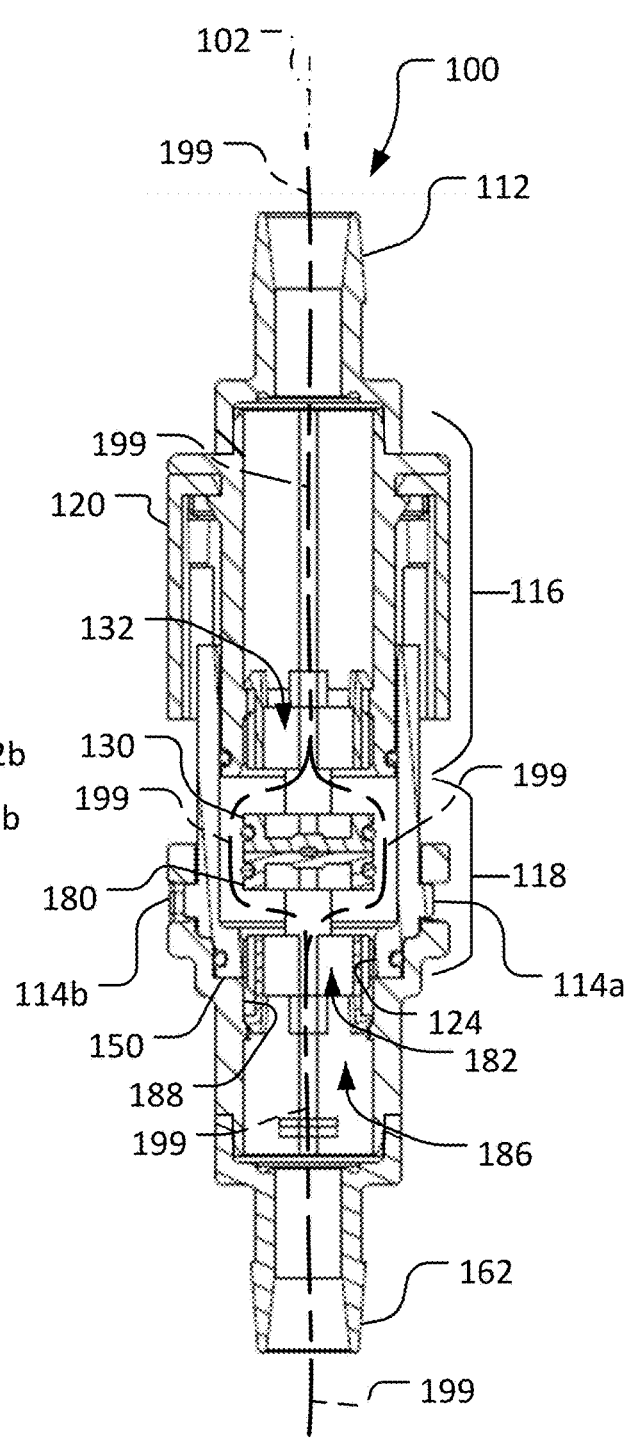
FIG. 6 is a longitudinal cross-sectional view of the fluid coupling device of FIG. 5.
Figure 7:
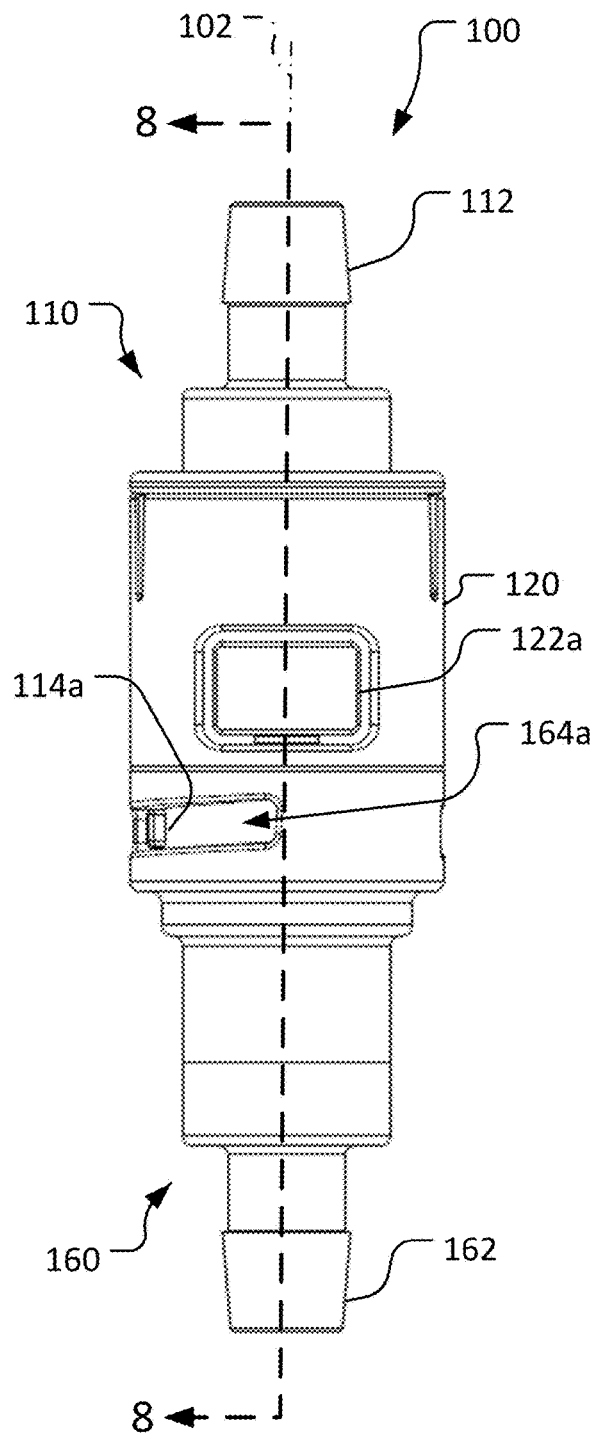
FIG. 7 is a first side view of the fluid coupling device of FIG. 3 with the coupling halves of the coupling device positioned in a longitudinally compressed arrangement (e.g., during a process of disconnecting the coupling halves from each other).
Figure 8:
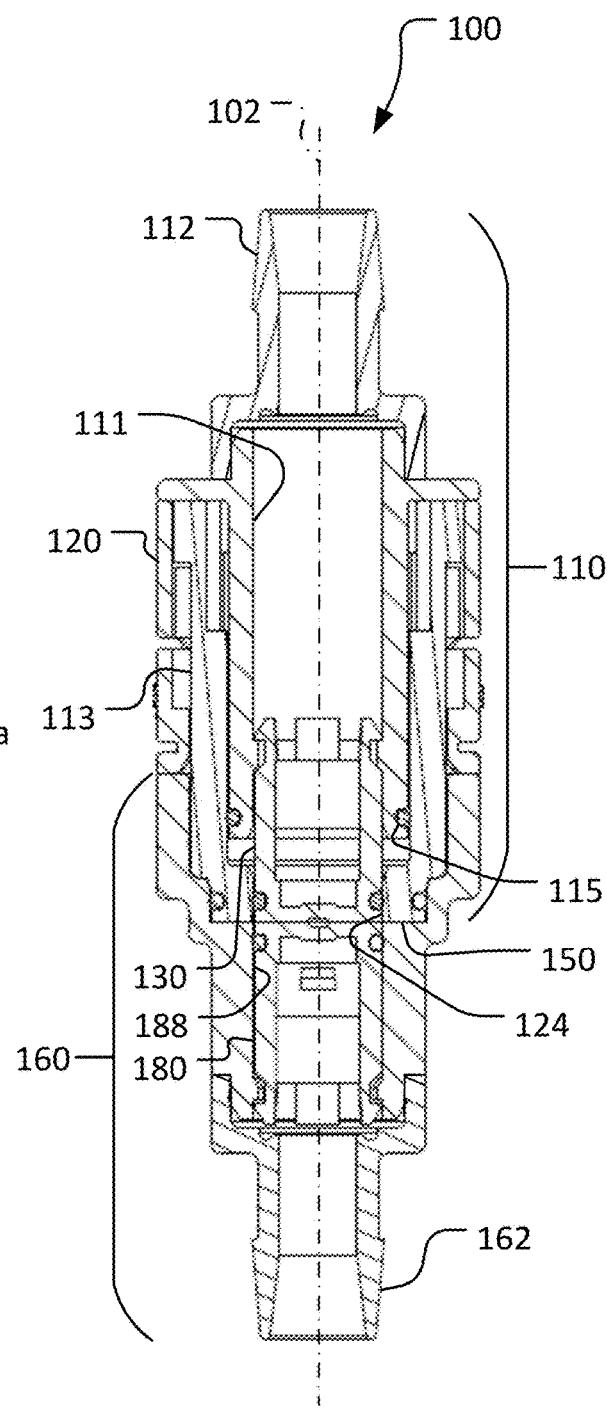
FIG. 8 is a longitudinal cross-sectional view of the fluid coupling device of FIG. 7.
Figure 9:
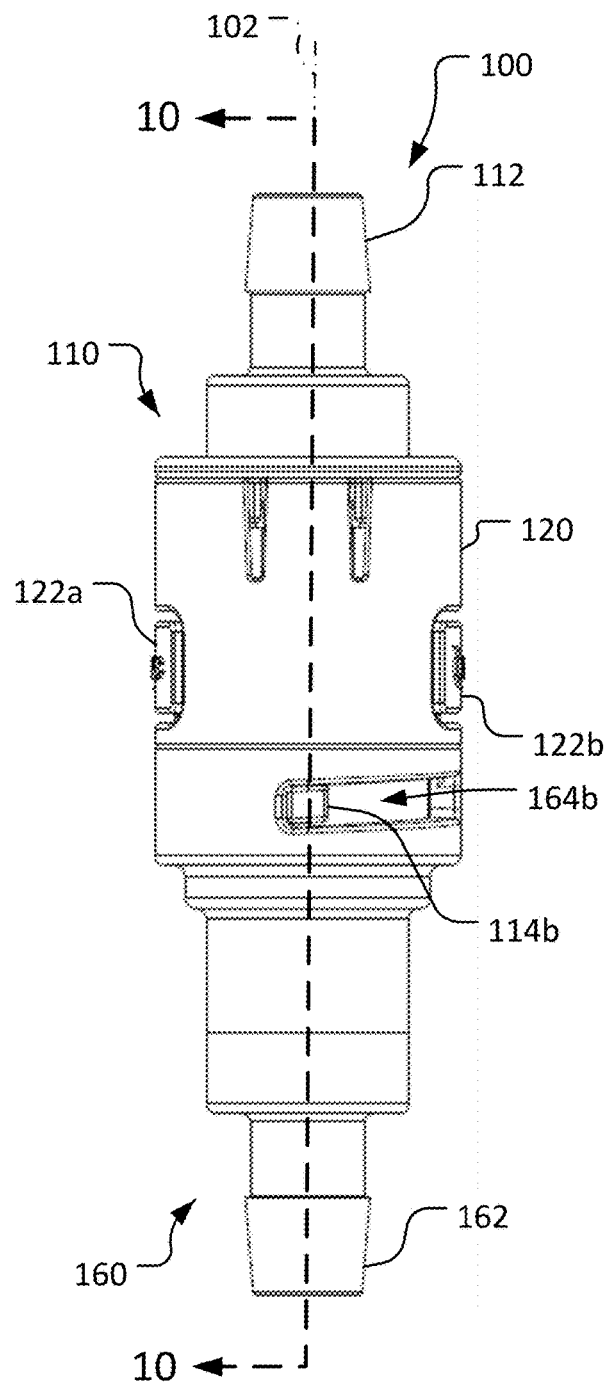
FIG. 9 is a second side view of the fluid coupling device of FIG. 7. The perspective of the second side view of FIG. 9 is 90° from the first side view of FIG. 7.
Figure 10:
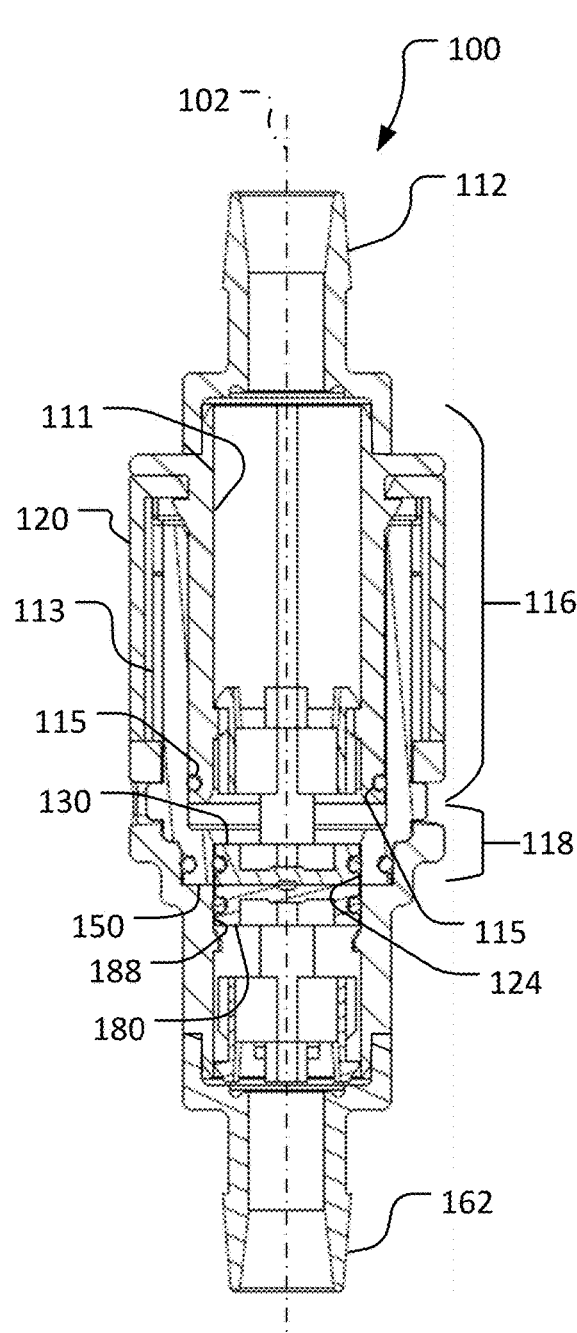
FIG. 10 is a longitudinal cross-sectional view of the fluid coupling device of FIG. 9.
Figure 13:
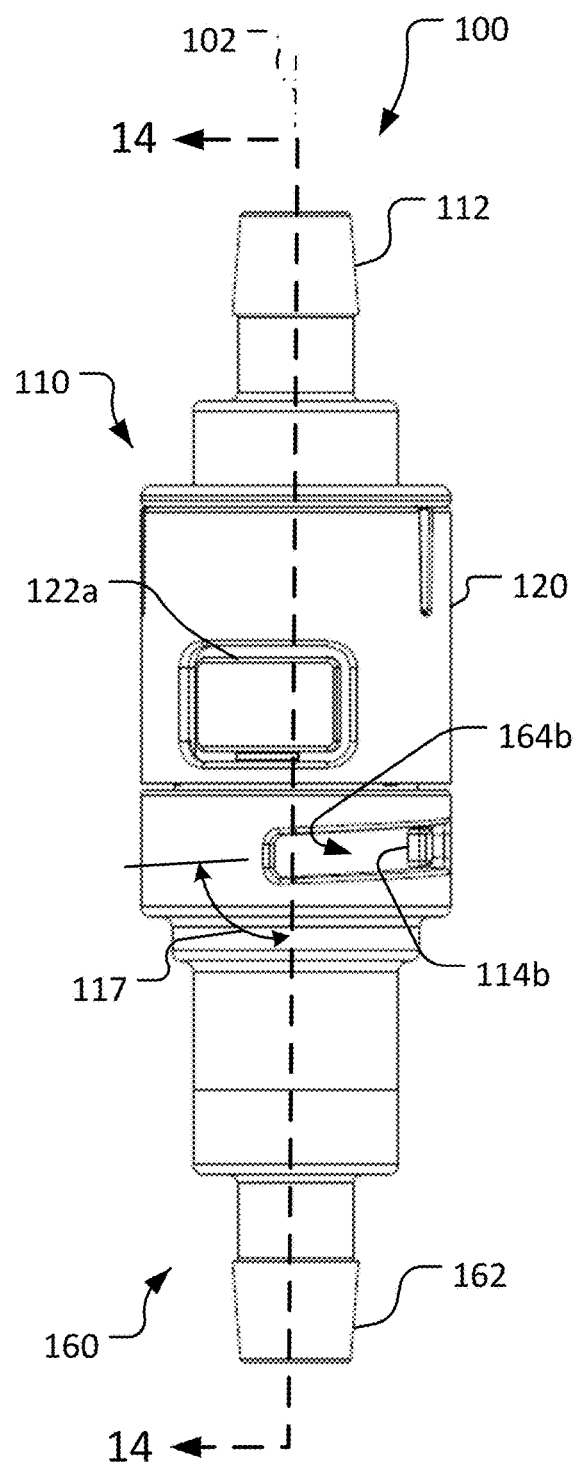
FIG. 13 is a second side view of the fluid coupling device of FIG. 11. The perspective of the second side view of FIG. 13 is 90° from the first side view of FIG. 11.

Referring to FIGS. 1 and 2, some example embodiments of a fluid system 10 include one or more example fluid coupling devices 100 configured to, for example, releasably connect a first fluid system equipment or container 20 to a second fluid system equipment or container 30. In some implementations, the fluid system 10 may include at least one fluid coupling device 100 that is a single-use, aseptic disconnection fluid coupling device, in which first and second mating components 110 and 160 are configured to disconnect from one another in a manner that provides an aseptic disconnection and that mechanically prevents reuse of the fluid path through the mating components 110 and 160. (The first and second mating portions 110 and 160 are sometimes referred to herein as "coupling halves" or a "coupling-half" even though the components 110 and 160 are not necessarily equal halves in terms of size, shape, or weight.) In one non-limiting example, the fluid coupling 100 can provide a single-use, aseptic disconnection capability for a fluid path between the fluid system equipment 20 in the form of a bioreactor system (connected directly to the coupling device 100 or connected via a fluid tube 22) and the fluid system container 30 in the form of a media bag (connected directly to the coupling device 100 or connected via a fluid tube 32).

Still referring to FIGS. 1 and 2, the fluid coupling 100 in the depicted embodiment includes the mating components 110 and 160 in the form a male coupling-half 110 and a female coupling-half 160. The male coupling-half 110 and the female coupling-half 160 are selectively matable to each other. The coupling halves 110 and 160 are shown coupled (connected) in FIG. 1. The coupling halves 110 and 160 are shown uncoupled (disconnected) from each other in FIG. 2. Each coupling-half 110 and 160, as well as the assembled coupling 100 overall, defines a longitudinal axis 102. Optionally, the male coupling-half 110 and the female coupling-half 160 are structured to be coupled using a bayonet-style connection. Accordingly, the male coupling-half 110 has two radially protruding posts 114a and 114b that are about 180° opposed from each other. The female coupling-half 160 has two corresponding slots 164a and 164b that can receive the radially protruding posts 114a and 114b. Each slot 164a and 164b has an end-of-slot-aperture through which the radially protruding posts 114a and 114b can enter the slots 164a and 164b respectively.

To initiate the coupling of the coupling halves 110 and 160, the radially protruding posts 114a and 114b must be oriented into alignment with the end-of-slot-apertures of the slots 164a and 164b. Then, the coupling halves 110 and 160 can be longitudinally pressed towards each other. In doing so, the radially protruding posts 114a and 114b enter into the slots 164a and 164b by passing through the end-of-slot-apertures of the slots 164a and 164b. Thereafter, the male coupling-half 110 can be rotated in relation to the female coupling-half 160. The rotation causes the radially protruding posts 114a and 114b to travel within the slots 164a and 164b respectively. The coupling process is completed when the male coupling-half 110 has been rotated in relation to the female coupling-half 160 to the extent that the radially protruding posts 114a and 114b reach the ends of the slots 164a and 164b that are opposite from the end-of-slot-apertures of the slots 164a and 164b. In some embodiments, the bayonet connection is structured such that about 90° of relative rotation between the male coupling-half 110 and the female coupling-half 160 will accomplish the bayonet-style coupling action.

In some embodiments, other types of coupling mechanisms and techniques are used for selectively coupling the male coupling-half 110 and the female coupling-half 160. For example, in some embodiments threaded connections, detent connections, clamp connections, and the like, are used to selectively couple the male coupling-half 110 with the female coupling-half 160.

While the coupling halves 110 and 160 are coupled as shown in FIG. 1, an open fluid flow path is established through the coupling 100. That is, in the operably coupled configuration, fluid can flow through the coupling 100 between a first connection 112 and a second connection 162.

While the coupling 100 is in its operably coupled configuration, structural elements of the coupling 100 lock the coupling halves 110 and 160 in their respective operable positions. Therefore, to disconnect the coupling halves 110 and 160 from each other, the user is required to perform an unlocking procedure.

In the depicted embodiment, the procedure to unlock the coupling 100 is performed by manipulating a locking sleeve 120 that is slidably coupled to the male coupling-half 110. Once the locking sleeve 120 has been slid (translated longitudinally) to a position near to the female coupling-half 160, then the user can rotate the coupling halves 110 and 160 in relation to each other to disengage the bayonet connection. Conversely, until the locking sleeve 120 is slid (translated longitudinally) to a position near to the female coupling-half 160, the coupling halves 110 and 160 cannot be rotated in relation to each other. Instead, the coupling halves 110 and 160 remain locked in the operably coupled configuration. That is the case at least because shuttle valve members within the coupling 100 have non-circular cross-sectional shapes, as described further below.

In the depicted embodiment, the locking sleeve 120 includes a first unlocking member 122a and a second unlocking member 122b (not visible). In some embodiments, the first unlocking member 122a and the second unlocking member 122b are oriented at about 180° in relation to each other on the locking sleeve 120. In the depicted embodiment, the unlocking members 122a and 122b must be simultaneously depressed in order to unlock the locking sleeve 120, so that it can then be slid from its orientation in the operably coupled configuration (as shown in FIG. 1) to a position near to the female coupling-half 160. In the depicted embodiment, unless both unlocking members 122a and 122b are depressed simultaneously, the locking sleeve 120 cannot be slid towards the female coupling-half 160.

In a summarized manner, the unlocking procedure of the depicted embodiment of coupling 100 is performed as follows. Beginning with the coupling 100 in the operably coupled configuration of FIG. 1, the user first simultaneously depresses the first and second unlocking members 122a and 122b. While maintaining the first and second unlocking members 122a and 122b in their depressed orientations, the user then slides the locking sleeve 120 towards the female coupling-half 160. When the unlocking sleeve 120 has been slid to its end of travel near the female coupling-half 160, then the user can rotate the coupling halves 110 and 160 in relation to each other to disengage the bayonet connection. The user can then longitudinally separate the coupling halves 110 and 160 as depicted in FIG. 2. It should be understood that this unlocking procedure, and the corresponding structural elements that facilitate this unlocking procedure, are merely examples of the kinds of unlocking procedures and structures that can be incorporated into various embodiments of the single-use, aseptic disconnection fluid coupling devices provided herein (of which the coupling 100 is one example).

While the coupling halves 110 and 160 are disconnected from each other as shown in FIG. 2, fluids are blocked from flowing through the coupling halves 110 and 160 individually. That is, in the disconnected configuration, even though a fluid source is connected to the first connection 112 and/or to the second connection 162, the fluid will not flow out of the coupling halves 110 and/or 160. That is the case because, as described further below, a shuttle valve member in each of the coupling halves 110 and 160 blocks fluid from flowing out of the coupling halves 110 and 160 while the coupling halves 110 and 160 are disconnected from each other.

The face of the male coupling shuttle valve member 130 is visible in FIG. 2. As shown, in the disconnected configuration the face of the male coupling shuttle valve member 130 is substantially flush with the end of the male coupling bore 124 in which the male coupling shuttle valve member 130 is slidably disposed.

As described further below, the shuttle valve members are individually slidable along a longitudinal path within bores of the coupling halves 110 and 160, between open and fully closed positions. While the shuttle valve members 130 and 180 are in their fully closed positions, fluid is blocked from flowing out of the coupling halves 110 and 160, and biological contaminants are blocked from entering into the fluid flow paths of the coupling halves 110 and 160. FIG. 2 provides an illustration of the male coupling shuttle valve member 130 positioned in its fully closed position such that fluid is blocked from flowing out of the male coupling-half 110, and biological contaminants are blocked from entering the fluid flow path of the male coupling-half 110. The female coupling-half 160 also has a shuttle valve member (not visible in FIG. 2) that functions in the same fashion as the male coupling shuttle valve member 130 within the male coupling-half 110.

In some embodiments, one or more of the shuttle valve members have non-circular cross-sectional shapes. For example, in the depicted embodiment the shuttle valve members 130 and 180 have ovular cross-sectional shapes (as illustrated by the male coupling shuttle valve member 130). As described further below, due to the ovular shape of the shuttle valve members 130 and 180, the coupling halves 110 and 160 cannot be rotated in relation to each other unless the shuttle valve members 130 and 180 are each longitudinally located in their fully closed position. Accordingly, the coupling halves 110 and 160 cannot be disconnected from each other unless the shuttle valve members 130 and 180 are each in their fully closed position. One of skill in the art will recognize that this structure prevents biological contamination of the fluid flow paths of the coupling halves 110 and 160 because the coupling halves 110 and 160 can only be disconnected from each other if the shuttle valve members 130 and 180 are each in their fully closed position. In addition, as described further below, when the shuttle valve members 130 and 180 are in their fully closed position, the shuttle valve members 130 and 180 are locked (detained) therein. Hence, coupling 100 is referred to herein as an aseptic disconnect coupling.

In the depicted embodiment, the first connection 112 and the second connection 162 are illustrated as barbed connections. It should be understood that the first connection 112 and/or the second connection 162 can be any type of connection including, but not limited to, threaded fittings, sanitary flanges, compression fittings, luer fittings, luer-lock fittings, and the like. In some embodiments, the first connection 112 and the second connection 162 are dissimilar types of connections. In some embodiments, the first connection 112 and/or the second connection 162 facilitate multiple points of connection (e.g., a Y-fitting, a T-fitting, a manifold, and the like).

In some embodiments, the materials from which the components of the coupling 100 are made of include thermoplastics. In particular embodiments, the materials from which the components of the coupling 100 are made of are biocompatible thermoplastics, such as, but not limited to, polycarbonate, polysulphone, polyether ether ketone, polysulphide, polyester, polyphenylene, polyaryletherketone, and the like, and combinations thereof. In some embodiments, the coupling 100 is metallic-free. That is, in some embodiments no metallic materials are included in the coupling 100. In some embodiments, no metallic springs are included in the coupling 100. In various embodiments, substantially no components of the coupling 100 (other than one or more seals) are under mechanical stress while the coupling 100 is in the operably coupled configuration. In some embodiments, the seals are made of materials such as, but not limited to, silicone, fluoroelastomers (FKM), ethylene propylene diene monomer (EPDM), and the like.

Referring to FIGS. 3-6, the coupling 100 can be oriented in an operably coupled configuration such that a fluid flow path 199 extends between the first connection 112 and the second connection 162. In the operably coupled configuration, as shown, the male coupling-half 110 and the female coupling-half 160 abut each other at a circumferential interface 150. An o-ring seal 152 between the male coupling-half 110 and the female coupling-half 160 near the circumferential interface 150 provides a fluid seal.

The coupling 100 includes the male coupling shuttle valve member 130 and the female coupling shuttle valve member 180. The shuttle valve members 130 and 180 are slidable in relation to the male coupling-half 110 and the female coupling-half 160, along the longitudinal axis 102 of the coupling 100.

In the operably coupled configuration, as shown, the male coupling shuttle valve member 130 and the female coupling shuttle valve member 180 are abutted, face-to-face, and are positioned longitudinally toward the male coupling-half 110. It can be said that, while in the operably coupled configuration, the male coupling shuttle valve member 130 and the female coupling shuttle valve member 180 are longitudinally biased towards the male coupling-half 110 because their abutting faces are positioned longitudinally away from the circumferential interface 150 towards the side of the male coupling-half 110.

The fluid flow through coupling 100 can be in the direction from the first connection 112 to the second connection 162, or vice versa. The coupling 100 is not limited to having the fluid flow therethrough in one particular direction. Rather, fluid can flow through coupling 100 in either direction.

The flow path 199 from the first connection 112 to the second connection 162 (i.e., from top to bottom in FIG. 4) passes through the coupling 100 as follows. Fluid enters the first connection 112 and passes into a first male coupling-half internal space 116 defined by the male coupling-half 110. The flow path 199 then enters into an internal male coupling shuttle valve member space 132 defined by the male coupling shuttle valve member 130. The flow path 199 then passes through one or more male coupling shuttle valve apertures 134 defined by the male coupling shuttle valve member 130 and into a second male coupling-half internal space 118 defined by the male coupling-half 110. The flow path 199 then passes through one or more female coupling shuttle valve apertures 184 defined by the female coupling shuttle valve member 180 and into an internal female coupling shuttle valve member space 182 defined by the female coupling shuttle valve member 180. The flow path 199 then enters a female coupling-half internal space 186 defined by the female coupling-half 180, and then passes out through the second connection 162.

The flow path 199 from the second connection 162 to the first connection 112 (i.e., from bottom to top in FIG. 4) passes through the coupling 100 as follows. Fluid enters the second connection 162 and passes into the female coupling-half internal space 186 defined by the female coupling-half 160. The flow path 199 then enters into the internal female coupling shuttle valve member space 182 defined by the female coupling shuttle valve member 180. The flow path 199 then passes through one or more female coupling shuttle valve apertures 184 defined by the female coupling shuttle valve member 180 and into the second male coupling-half internal space 118 defined by the male coupling-half 110. The flow path 199 then passes through one or more male coupling shuttle valve apertures 134 defined by the male coupling shuttle valve member 130 and into the internal male coupling shuttle valve member space 132 defined by the male coupling shuttle valve member 130. The flow path 199 then enters the first male coupling-half internal space 116 defined by the male coupling-half 110, and then passes out through the first connection 112.

In some embodiments, the first connection 112 and/or the second connection 162 are formed integrally with the other portions of the male coupling-half 110 and/or the female coupling-half 160. Alternatively, in some embodiments the first connection 112 and/or the second connection 162 are formed separately from other portions of the male coupling-half 110 and/or the female coupling-half 160, and then subsequently affixed to the other portions of the male coupling-half 110 and/or the female coupling-half 160 respectively. Such a manufacturing technique can be referred to as modular construction. Joining techniques such as, but not limited to, ultrasonic welding, laser welding, solvent bonding, gluing, overmolding, insert molding, and the like, and combinations thereof, can be used to affix the first connection 112 and/or the second connection 162 with the other portions of the male coupling-half 110 and/or the female coupling-half 160.

In the operably coupled configuration as shown, the coupling halves 110 and 160 cannot be rotated in relation to each other. That is the case because the female coupling shuttle valve member 180 (that has a non-circular cross-sectional shape) extends within the male coupling bore 124 and within a female coupling bore 188. The bores of the male coupling bore 124 and the female coupling bore 188 have non-circular cross-section shapes that correspond to the non-circular cross-sectional shape of the female coupling shuttle valve member 180. Hence, the coupling halves 110 and 160 cannot be rotated in relation to each other.

In the depicted embodiment, the female coupling shuttle valve member 180 has an ovular cross-sectional shape, and both the male coupling bore 124 and the female coupling bore 188 have ovular cross-sectional shapes that correspond to the ovular cross-sectional shape of the female coupling shuttle valve member 180. This arrangement provides a keyed relationship between the coupling halves 110 and 160, with the female coupling shuttle valve member 180 being the key. Hence, the coupling halves 110 and 160 cannot be rotated in relation to each other.

In the operably coupled configuration as shown, the locking sleeve 120 is locked in its longitudinal position on the male coupling-half 110. As described above, the unlocking members 122a and 122b must be simultaneously depressed in order to unlock the locking sleeve 120 so that it can then be slid from its orientation in the operably coupled configuration to a position near to the female coupling-half 160. Unless both unlocking members 122a and 122b are depressed, the locking sleeve 120 cannot be slid towards the female coupling-half 160.

It should be understood from the foregoing description that, while the coupling 100 is in the operably coupled configuration, no reconfiguration of the coupling 100 is likely to occur unintentionally. That is the case, for example, because the coupling halves 110 and 160 cannot be rotated in relation to each other, and because the locking sleeve 120 cannot be slid from its orientation in the operably coupled configuration unless the unlocking members 122a and 122b are simultaneously depressed. Hence, without intentional actions of a user, the coupling 100 will steadfastly remain in its operably coupled configuration.

The arrangement and operation of the coupling 100 in its operably coupled configuration has now been described. The following figures and description will provide step-by-step details of techniques for disconnecting the male coupling-half 110 from the female coupling-half 160. It should be understood from the following figures and description that the structure of the coupling 100 ensures that the coupling 100 provides a single-use, aseptic disconnection fluid coupling device that substantially prevents fluid discharge when being disconnected.

Referring to FIGS. 7-10, for the depicted embodiment of coupling 100, the technique for disconnection of the male coupling-half 110 from the female coupling-half 160 begins with unlocking the locking sleeve 120 and then sliding the locking sleeve 120 towards the female coupling-half 160. These figures show the position of the locking sleeve 120 after the locking sleeve 120 has been unlocked and slid fully towards the female coupling-half 160.

In the depicted embodiment, the locking sleeve 120 cannot be slid longitudinally towards the female coupling-half 160 until the unlocking members 122a and 122b are both simultaneously held in a depressed arrangement. In some embodiments, other types of unlocking mechanisms are used.

While the unlocking members 122a and 122b are both simultaneously held in a depressed arrangement, the locking sleeve 120 can be slid longitudinally towards the female coupling-half 160. As the locking sleeve 120 slides towards the female coupling-half 160, an inner male coupling-half barrel member 111 slides within an outer male coupling-half barrel member 113 that remains stationary. The inner male coupling-half barrel member 111 is coupled with the locking sleeve 120. Consequently, the inner male coupling-half barrel member 111 moves in conjunction with the locking sleeve 120. The outer male coupling-half barrel member 113 remains stationary in relation to the female coupling-half 160 while the locking sleeve 120 and the inner male coupling-half barrel member 111 are translated longitudinally towards the female coupling-half 160. An o-ring seal 115 is disposed between the inner male coupling-half barrel member 111 and the outer male coupling-half barrel member 113 to provide a fluid seal therebetween.

As the locking sleeve 120 and the inner male coupling-half barrel member 111 are translated longitudinally towards the female coupling-half 160, the male coupling shuttle valve member 130 also translates longitudinally towards the female coupling-half 160. That is the case because the male coupling shuttle valve member 130 is coupled to the inner male coupling-half barrel member 111. Moreover, because the male coupling shuttle valve member 130 is abutted face-to-face with the female coupling shuttle valve member 180, the female coupling shuttle valve member 180 is also forced to translate longitudinally towards the female coupling-half 160.

The locking sleeve 120 is translated longitudinally towards the female coupling-half 160 until the position of the face-to-face abutment of the male coupling shuttle valve member 130 and the female coupling shuttle valve member 180 is longitudinally aligned with the circumferential interface 150 between the coupling halves 110 and 160. This is the arrangement shown in FIGS. 7-10. When the shuttle valve members 130 and 180 reach the arrangement shown in FIGS. 7-10, both of the shuttle valve members 130 and 180 become detained in those respective positions (where the face-to-face abutment of the shuttle valve members 130 and 180 is longitudinally aligned with the circumferential interface 150).

The arrangement shown in FIGS. 7-10 results in a blockage of the previously existing flow path 199 (refer to FIGS. 3-6). That is, when the locking sleeve 120 is slid longitudinally to its end-of-travel position near to the female coupling-half 160 (as shown in FIGS. 7-10), a flow path no longer exists between the first connection 112 and the second connection 162. Rather, the longitudinal sliding of the locking sleeve 120 to its end-of-travel position near to the female coupling-half 160 (as shown in FIGS. 7-10) eliminates the previously existing flow path 199 between the first connection 112 and the second connection 162. What is more, because both of the shuttle valve members 130 and 180 become detained in their respective positions (as shown in FIGS. 7-10), the previously existing flow path 199 cannot be reestablished after the locking sleeve 120 is slid longitudinally to its end-of-travel position near to the female coupling-half 160. Rather, the flow path 199 through coupling 100 is permanently blocked. Hence, coupling 100 is referred to as a single-use coupling.

As described above, prior to sliding the locking sleeve 120 to configure the coupling 100 in the arrangement shown in FIGS. 7-10, the female coupling shuttle valve member 180 extended within the male coupling bore 124 and within the female coupling bore 188. Said differently, the female coupling shuttle valve member 180 (that has a non-circular cross-sectional shape) straddled the circumferential interface 150 between the coupling halves 110 and 160. In that arrangement, the coupling halves 110 and 160 could not be rotated in relation to each other.

In the arrangement shown in FIGS. 7-10, however, the female coupling shuttle valve member 180 is no longer straddling the circumferential interface 150 between the coupling halves 110 and 160. Rather, the face-to-face abutment of the male coupling shuttle valve member 130 and the female coupling shuttle valve member 180 is longitudinally aligned with the circumferential interface 150 between the coupling halves 110 and 160. Consequently, rotation between the coupling halves 110 and 160 is no longer structurally prevented.

Referring to FIGS. 11-14, the next step in the process for disconnecting the coupling halves 110 and 160 from each other is rotation of the coupling halves 110 and 160 in relation to each other. Such a rotation will partly disengage the bayonet connection mechanism between the coupling halves 110 and 160. FIGS. 11-14 show the coupling halves 110 and 160 after the rotation has been completed.

As the coupling halves 110 and 160 are rotated in relation to each other, the two radially protruding posts 114a and 114b slide within the two corresponding slots 164a and 164b. In some embodiments, such as the depicted embodiment, the slots 164a and 164b are not orthogonal with the longitudinal axis 102. Rather, in the depicted embodiment the slots 164a and 164b extend at a non-orthogonal angle 117 in relation to the longitudinal axis 102. In some embodiments, the non-orthogonal angle 117 is in a range from about 85° to about 90°, or about 80° to about 90°, or about 75° to about 85°, or about 70° to about 80°. In some embodiments, the slots 164a and 164b are generally orthogonal to the longitudinal axis 102.

Because the slots 164a and 164b of the depicted embodiment extend along the non-orthogonal angle 117, as the coupling halves 110 and 160 are rotated in relation to each other the coupling halves 110 and 160 will also translate longitudinally in relation to each other. That is, as the two radially protruding posts 114a and 114b are slid within the two corresponding slots 164a and 164b along the non-orthogonal angle 117 by the relative twisting of the coupling halves 110 and 160, the two radially protruding posts 114a and 114b travel longitudinally and cause the male coupling-half 110 to also travel longitudinally (in relation to the female coupling-half 160). Hence, the coupling halves 110 and 160 become slightly longitudinally separated from each other as the coupling halves 110 and 160 are rotated in relation to each other. This separation is visible in FIGS. 12 and 14 at the circumferential interface 150. A gap exists there between the male coupling-half 110 and the female coupling-half 160 where the two previously directly abutted each other.

The structures that result in the coupling halves 110 and 160 becoming slightly separated from each other as the coupling halves 110 and 160 are rotated in relation to each other can be advantageous in some cases. For example, the resulting slight separation may be advantageous for breaking a seal (or vacuum) that may exist between the coupling halves 110 and 160, and that may otherwise be difficult or inconvenient for a user to break.

Figure 14:
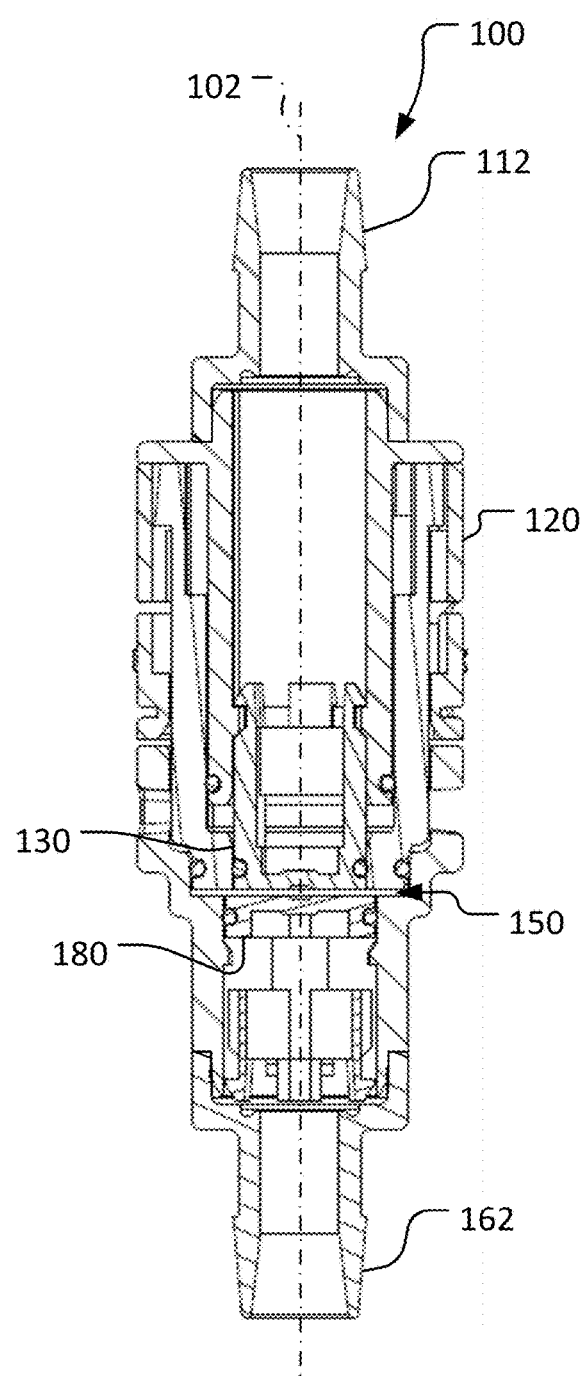
FIG. 14 is a longitudinal cross-sectional view of the fluid coupling device of FIG. 13.
Figure 17:
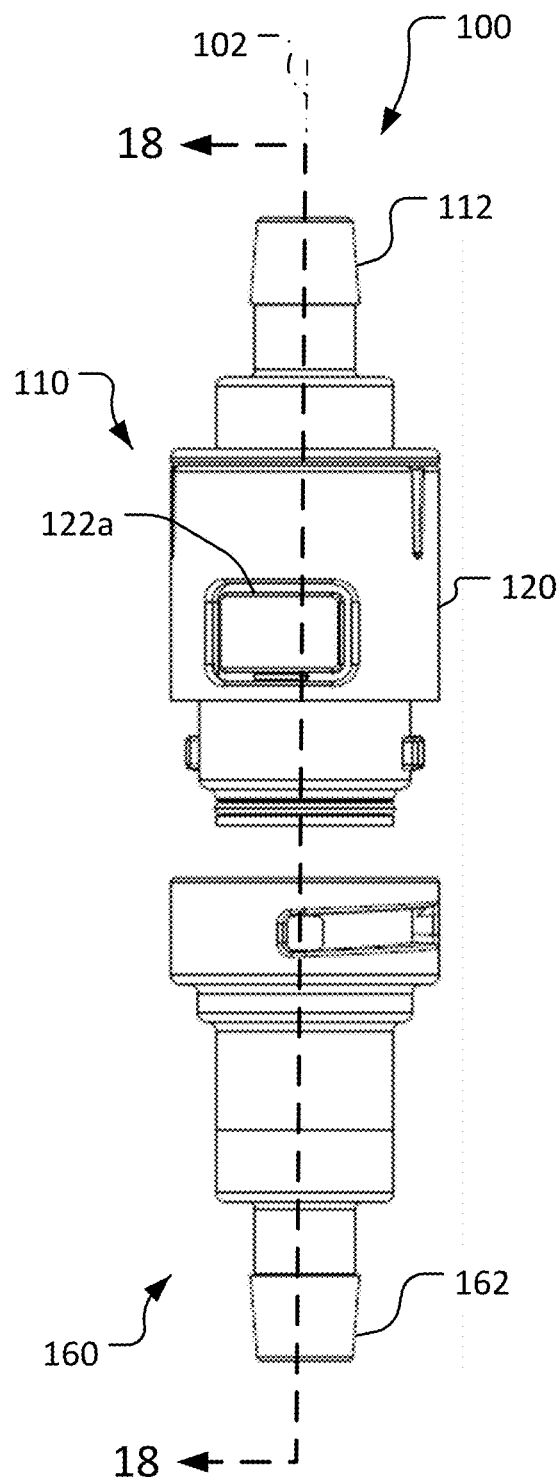
FIG. 17 is a second side view of the fluid coupling device of FIG. 15. The perspective of the second side view of FIG. 17 is 90° from the first side view of FIG. 15.

It is also apparent, by close observation near the area of the circumferential interface 150 in FIGS. 12 and 14, that the male coupling shuttle valve member 130 and the female coupling shuttle valve member 180 appear to have differing diameters. That appears to be the case in FIGS. 12 and 14 because, as described above, the male coupling shuttle valve member 130 and the female coupling shuttle valve member 180 have non-circular cross-sectional shapes (ovular cross-sectional shapes in the depicted embodiment). The relative rotation between the coupling halves 110 and 160 also rotates the male coupling shuttle valve member 130 in relation to the female coupling shuttle valve member 180. Hence, because of the perspective of the figures, the male coupling shuttle valve member 130 appears wider than the female coupling shuttle valve member 180 in FIG. 12, and the male coupling shuttle valve member 130 appears narrower than the female coupling shuttle valve member 180 in FIG. 14. In reality, in the depicted embodiment the male coupling shuttle valve member 130 and the female coupling shuttle valve member 180 have ovular cross-sectional shapes that are dimensionally equal to each other. Further, in some embodiments the male coupling shuttle valve member 130 and the female coupling shuttle valve member 180 are two of the very same physical design (shape), and are arranged as mirror images of each other (face-to-face) in the assembled coupling 100.

As described above, each slot 164a and 164b has an end-of-slot-aperture through which the radially protruding posts 114a and 114b can pass, respectively. In the arrangement of FIGS. 11-14, the radially protruding posts 114a and 114b are longitudinally aligned with the end-of-slot-apertures of slots 164a and 164b respectively.

Referring to FIGS. 15-18, the coupling halves 110 and 160 of coupling 100 can be disconnected (uncoupled) from each other. With the radially protruding posts 114a and 114b longitudinally aligned with the end-of-slot-apertures of slots 164a and 164b respectively, the male coupling-half 110 can be separated from the female coupling-half 160 by simply pulling them apart longitudinally.

Figure 18:
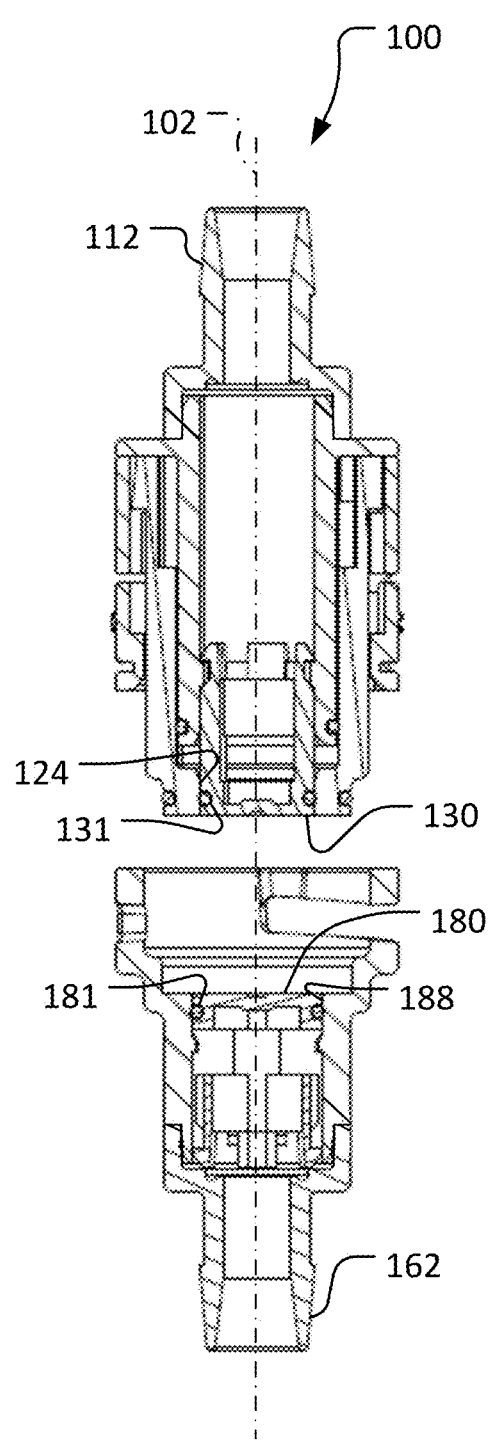
FIG. 18 is a longitudinal cross-sectional view of the fluid coupling device of FIG. 17.

FIGS. 16 and 18 illustrate that, when the coupling halves 110 and 160 are disconnected from each other, the face of the male coupling shuttle valve member 130 is substantially flush with the end of the male coupling bore 124. Similarly, the face of the female coupling shuttle valve member 180 is substantially flush with the end of the female coupling bore 188. In addition, FIGS. 16 and 18 illustrate that an o-ring 131 is positioned between the male coupling shuttle valve member 130 and the male coupling bore 124, near to the end of the male coupling bore 124. Similarly, an o-ring 181 is positioned between the female coupling shuttle valve member 180 and the female coupling bore 188, near to the end of the female coupling bore 188.

The arrangement where the face of the male coupling shuttle valve member 130 is substantially flush with the end of the male coupling bore 124, and the o-ring 131 is near to the end of the male coupling bore 124, inhibits or substantially prevents biological contamination from entering the male coupling-half 110. Similarly, the arrangement where the face of the female coupling shuttle valve member 180 is substantially flush with the end of the female coupling bore 188, and the o-ring 181 is near to the end of the female coupling bore 188, inhibits or substantially prevents biological contamination from entering the female coupling-half 160. In other words, these structural features make coupling 100 an aseptic disconnection fluid coupling device.

In addition, the aforementioned arrangement regarding the faces of the coupling shuttle valve members 130 and 180 being substantially flush with the ends of the coupling bores 124 and 188, and the o-rings 131 and 181 being near to the ends of the coupling bores 124 and 188 substantially prevents fluid discharge when the coupling halves 100 and 160 are being disconnected from each other.

When the coupling halves 110 and 160 have been disconnected from each other using the process described above, particular components of the coupling 100 are detained (effectively locked) in their respective positions. For example, the shuttle valve members 130 and 180 are detained in relation to the coupling bores 124 and 188. In addition, the locking sleeve 120 is detained in its position longitudinally on the male coupling-half 110. Hence, even if the bayonet connection between the coupling halves 110 and 160 is restored, the flow path through coupling 100 will not be reopened. For this reason, the coupling 100 is termed as a single-use coupling device. In other words, once the coupling halves 110 and 160 have been disconnected from each other, the coupling halves 100 and 160 cannot be reconnected so as to create a flow path through the coupling 100.

The inventive concepts provided herein pertaining to single-use, aseptic disconnection fluid coupling devices can be further illustrated in the context of additional example embodiments. For example, FIGS. 19-35 illustrate another example single-use, aseptic disconnection fluid coupling device 200 in accordance with some embodiments. Many of the functional characteristics of fluid coupling device 100 that make it a single-use, aseptic disconnection fluid coupling device are also shared by the aseptic disconnection fluid coupling device 200. However, some of the particular mechanisms that facilitate the functionality of coupling device 200 as a single-use, aseptic disconnection fluid coupling device are in different from the particular mechanisms of coupling device 100. This illustrates that many different types of mechanisms can be alternatively or additionally incorporated in the single-use, aseptic disconnection fluid coupling devices provided herein, and such variations are within the scope of the present disclosure.

Figure 19:
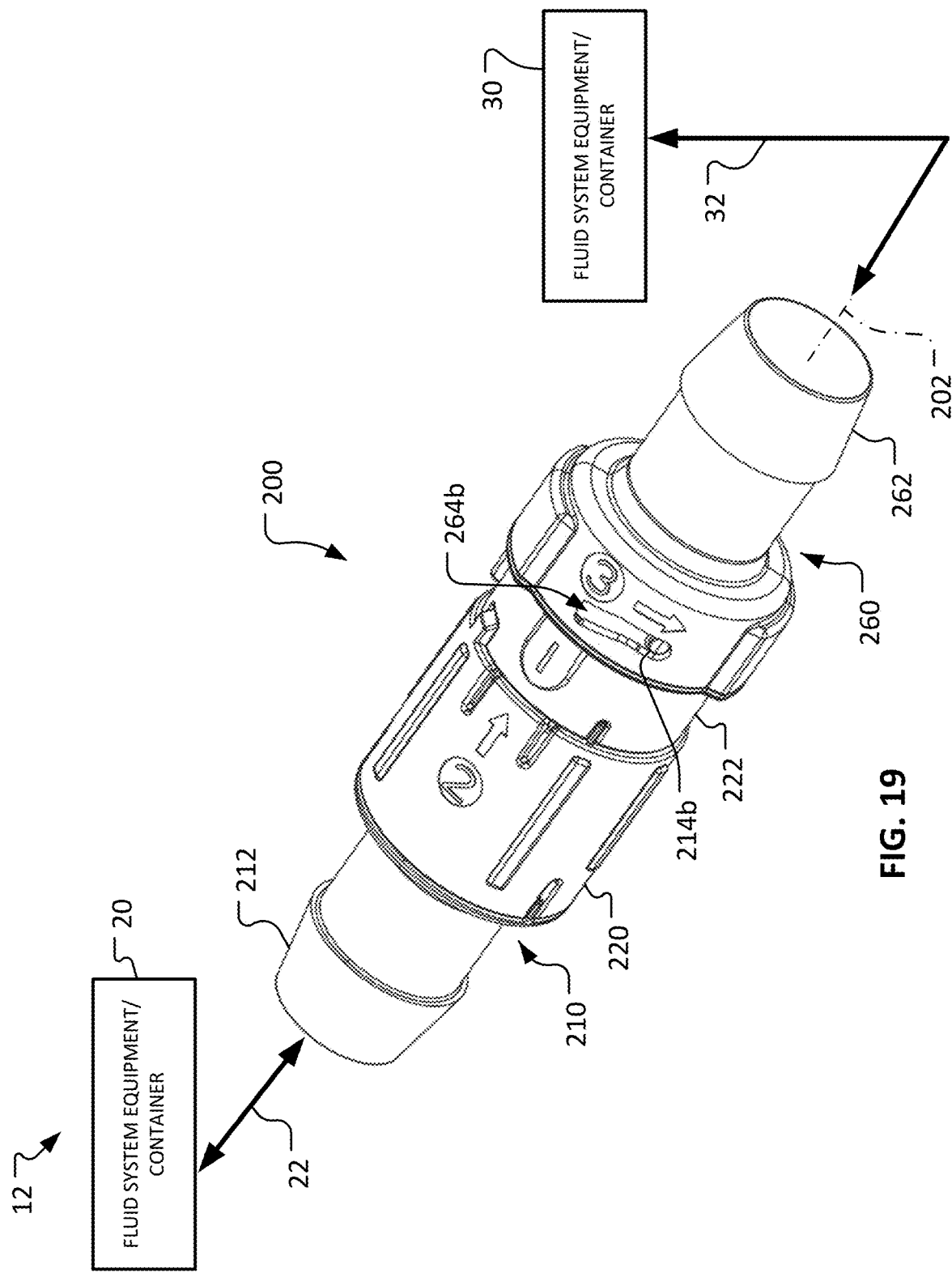
FIG. 19 is a perspective view of another example fluid system including another example fluid coupling device arranged in a connected configuration, in accordance with some embodiments provided herein.

FIG. 19 illustrates another example fluid system 12 that can include one or more example fluid coupling devices 200 configured to, for example, releasably connect the first fluid system equipment or container 20 to the second fluid system equipment or container 30. In some implementations, the fluid system 12 may include at least one fluid coupling device 200 that is a single-use, aseptic disconnection fluid coupling device, in which first and second mating components 210 and 260 are configured to disconnect from one another in a manner that provides an aseptic disconnection, and that mechanically prevents reuse of the fluid path through the mating components 210 and 260. (The first and second mating portions 210 and 260 are sometimes referred to herein as "coupling halves" or a "coupling-half" even though the components 210 and 260 are not necessarily equal halves in terms of size, shape, or weight.) In one non-limiting example, the fluid coupling 200 can provide a single-use, aseptic disconnection capability for a fluid path between the fluid system equipment 20 in the form of a bioreactor system (connected directly to the coupling device 200 or connected via a fluid tube 22) and the fluid system container 30 in the form of a media bag (connected directly to the coupling device 200 or connected via a fluid tube 32).

Figure 20:
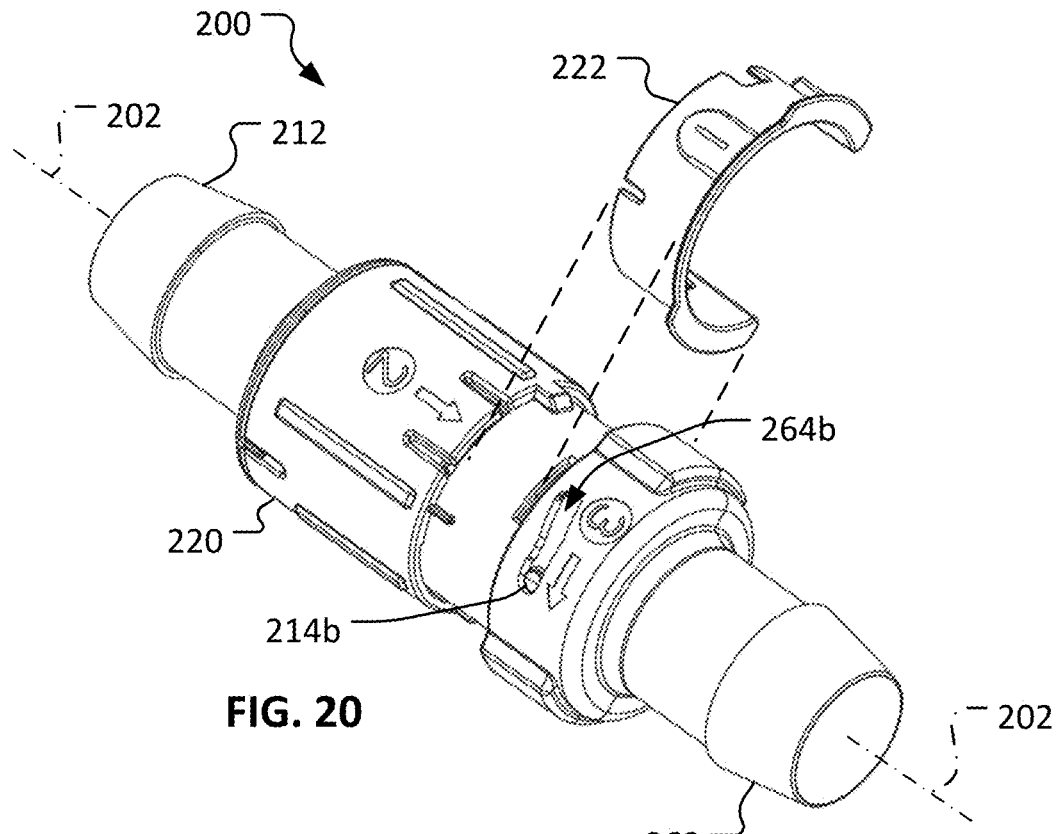
FIG. 20 is an exploded perspective view of the fluid coupling device of FIG. 19 with a locking collar separated from the rest of the fluid coupling device in preparation for disconnection of the fluid coupling device.
Figure 21:
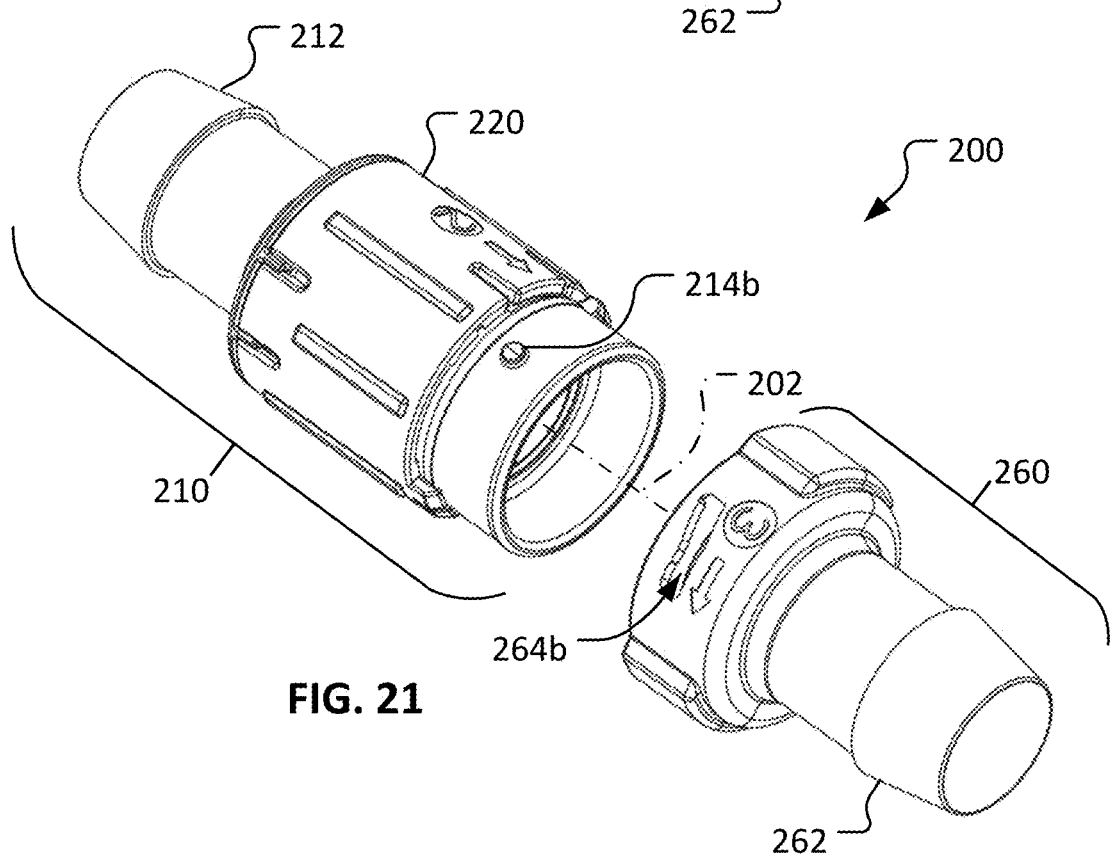
FIG. 21 is a perspective view of the fluid coupling device of FIG. 19 arranged in a disconnected configuration.
Figure 22:
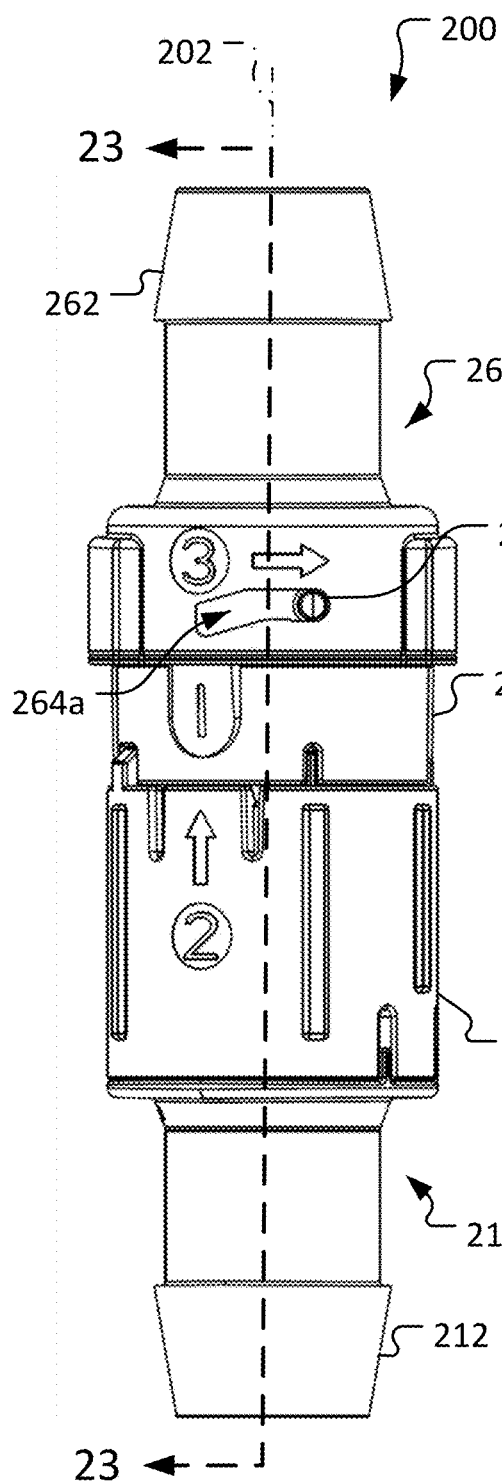
FIG. 22 is a first side view of the fluid coupling device of FIG. 19 with two coupling halves of the coupling device being arranged in a connected and operable configuration.

Referring also to FIGS. 20 and 21, the fluid coupling 200 in the depicted embodiment includes the mating components 210 and 260 in the form a male coupling-half 210 and a female coupling-half 260. The male coupling-half 210 and the female coupling-half 260 are selectively matable to each other. The coupling halves 210 and 260 are shown coupled (connected) in FIGS. 19 and 20. The coupling halves 210 and 260 are shown uncoupled (disconnected) from each other in FIG. 21. Each coupling-half 210 and 260, as well as the assembled coupling 200 overall, defines a longitudinal axis 202. Optionally, the male coupling-half 210 and the female coupling-half 260 are structured to be coupled using a bayonet-style connection. Accordingly, the male coupling-half 210 has two radially protruding posts 214a and 214b that are about 180° opposed from each other. The female coupling-half 260 has two corresponding slots 264a and 264b that can receive the radially protruding posts 214a and 214b. Each slot 264a and 264b has an end-of-slot-aperture through which the radially protruding posts 214a and 214b can enter the slots 264a and 264b respectively.

To initiate the coupling of the coupling halves 210 and 260, the radially protruding posts 214a (not visible) and 214b must be oriented into alignment with the end-of-slot-apertures of the slots 264a (not visible) and 264b. Then, the coupling halves 210 and 260 can be longitudinally advanced towards each other. In doing so, the radially protruding posts 214a and 214b enter into the slots 264a and 264b by passing through the end-of-slot-apertures of the slots 264a and 264b.

Thereafter, the male coupling-half 210 can be rotated in relation to the female coupling-half 260. The rotation causes the radially protruding posts 214*a* and 214*b* to travel within the slots 264*a* and 264*b* respectively. The coupling process is completed when the male coupling-half 210 has been rotated in relation to the female coupling-half 260 to the extent that the radially protruding posts 214*a* and 214*b* reach the ends of the slots 264*a* and 264*b* that are opposite from the end-of-slot-apertures of the slots 264*a* and 264*b*. In some embodiments, the bayonet connection is structured such that about 90° of relative rotation between the male coupling-half 210 and the female coupling-half 260 will accomplish the bayonet-style coupling action. In some embodiments, the bayonet connection is structured such that about 80°, or about 70°, or about 60°, or about 50°, or about 45°, or about 40°, or about 30°, or less than 30° of relative rotation between the male coupling-half 210 and the female coupling-half 260 will accomplish the bayonet-style coupling action.

In some embodiments, other types of coupling mechanisms and techniques are used for selectively coupling the male coupling-half 210 and the female coupling-half 260. For example, in some embodiments threaded connections, detent connections, clamp connections, and the like, are used to selectively couple the male coupling-half 210 with the female coupling-half 260.

While the coupling halves 210 and 260 are coupled as shown in FIGS. 19 and 20, an open fluid flow path is established through the coupling 200. That is, in the operably coupled configuration, fluid can flow through the coupling 200 between a first connection 212 and a second connection 262. The open fluid flow path established through the coupling 200 is sealed. Accordingly, liquid(s) that are flowing through the coupling 200 are isolated from the environment outside of the fluid flow path, and the environment outside of the fluid flow path is isolated from the liquid(s) that are flowing through the coupling 200. Hence, the coupling 200 is configured to operate as an aseptic coupling, and the sterility of the fluid flow path (in cases where the fluid flow path is sterile prior to use) can be maintained even if the environment outside of the fluid flow path is non-sterile.

While the coupling 200 is in its operably coupled configuration, structural elements of the coupling 200 releasably lock the coupling halves 210 and 260 in their respective operable positions. Therefore, to disconnect the coupling halves 210 and 260 from each other, the user is required to perform an unlocking procedure.

In the depicted embodiment, the procedure to unlock the coupling 200 is performed by manipulating a locking sleeve 220 that is slidably coupled to the male coupling-half 210. Once the locking sleeve 220 has been slid (translated longitudinally) to a position near to the female coupling-half 260, then the user can rotate the coupling halves 210 and 260 in relation to each other to disengage the bayonet connection. Conversely, until the locking sleeve 220 is slid (translated longitudinally) to a position near to the female coupling-half 260, the coupling halves 210 and 260 cannot be rotated in relation to each other. Instead, the coupling halves 210 and 260 remain locked in the operably coupled configuration.

In the depicted embodiment, the locking sleeve 220 can be physically obstructed from sliding toward the female coupling-half 260 by the presence of a removable locking collar 222 that is latchable in the space between the locking sleeve 220 and the female coupling-half 260 as illustrated in FIG. 19. The locking collar 222 can have various configurations. For example, as illustrated in FIG. 20, in the depicted embodiment the locking collar 222 is a c-shaped element that is elastically flexible to facilitate convenient installation and/or removal of the locking collar 222 from its designated position between the locking sleeve 220 and the female coupling-half 260. To decouple the coupling halves 210 and 260, the locking collar 222 can be removed so that the locking sleeve 220 can then be longitudinally translated toward the female coupling-half 260.

In a summarized manner, the unlocking procedure of the depicted embodiment of coupling 200 is performed as follows. Beginning with the coupling 200 in the operably coupled configuration of FIG. 19, the user first removes the locking collar 222 as depicted in FIG. 20. The user then slides the locking sleeve 220 towards the female coupling-half 260. When the unlocking sleeve 220 has been slid to its end of travel near the female coupling-half 260, then the user can rotate the coupling halves 210 and 260 in relation to each other to disengage the bayonet connection. The user can then longitudinally separate the coupling halves 210 and 260 as depicted in FIG. 21. It should be understood that this unlocking procedure, and the corresponding structural elements that facilitate this unlocking procedure, are merely examples of the kinds of unlocking procedures and structures that can be incorporated into various embodiments of the single-use, aseptic disconnection fluid coupling devices provided herein (of which the coupling 200 is one example).

While the coupling halves 210 and 260 are disconnected from each other as shown in FIG. 21, fluids are blocked from flowing through the coupling halves 210 and 260 individually. That is, in the disconnected configuration, even though a fluid source is connected to the first connection 212 and/or to the second connection 262, the fluid will not flow out of the coupling halves 210 and/or 260. That is the case because, as described further below, a shuttle valve member in each of the coupling halves 210 and 260 blocks fluid from flowing out of the coupling halves 210 and 260 while the coupling halves 210 and 260 are disconnected from each other.

As described further below, the shuttle valve members are individually slidable along a longitudinal path within bores of the coupling halves 210 and 260, between open and fully closed positions. While the shuttle valve members 230 and 280 are in their fully closed positions (and during the process of decoupling the coupling halves 210 and 260 which moves the shuttle valve members 230 and 280 to their fully closed positions), fluid is blocked from flowing out of the coupling halves 210 and 260, and biological contaminants are blocked from entering into the fluid flow paths of the coupling halves 210 and 260. In the depicted embodiment of coupling 200, the shuttle valve members 230 and 280 have circular cross-sectional shapes (as opposed to the ovular shapes of the shuttle valve members 130 and 180 described above in reference to coupling 100).

In the depicted embodiment, the first connection 212 and the second connection 262 are illustrated as barbed connections. It should be understood that the first connection 212 and/or the second connection 262 can be any type of connection including, but not limited to, threaded fittings, sanitary flanges, compression fittings, luer fittings, luer-lock fittings, and the like. In some embodiments, the first connection 212 and the second connection 262 are dissimilar types of connections. In some embodiments, the first connection 212 and/or the second connection 262 facilitate multiple points of connection (e.g., a Y-fitting, a T-fitting, a manifold, and the like).

In some embodiments, the materials from which the components of the coupling 200 are made of include thermoplastics. In particular embodiments, the materials from which the components of the coupling 200 are made of are biocompatible thermoplastics, such as, but not limited to, polycarbonate, polysulfone, polyether ether ketone, polysulphide, polyester, polyphenylene, polyaryletherketone, and the like, and combinations thereof. In some embodiments, the coupling 200 is metallic-free. That is, in some embodiments no metallic materials are included in the coupling 200. In some embodiments, no metallic springs are included in the coupling 200. In various embodiments, substantially no components of the coupling 200 (other than stresses associated with the one or more seals) are under mechanical stress while the coupling 200 is in the operably coupled configuration. In some embodiments, the seals are made of materials such as, but not limited to, silicone, fluoroelastomers (FKM), ethylene propylene diene monomer (EPDM), and the like.

Referring to FIGS. 22-25, the coupling 200 can be oriented in an operably coupled configuration such that a fluid flow path 299 extends between the first connection 212 and the second connection 262. In the operably coupled configuration, as shown, the male coupling-half 210 and the female coupling-half 260 abut each other at a circumferential interface 250. An o-ring seal 252 between the male coupling-half 210 and the female coupling-half 260 near the circumferential interface 250 provides a fluid seal.

The coupling 200 includes the male coupling shuttle valve member 230 and the female coupling shuttle valve member 280. The shuttle valve members 230 and 280 are slidable in relation to the male coupling-half 210 and the female coupling-half 260, along the longitudinal axis 202 of the coupling 200. In the depicted embodiment, the shuttle valve members 230 and 280 have circular cross-sectional shapes.

In the operably coupled configuration, as shown, the male coupling shuttle valve member 230 and the female coupling shuttle valve member 280 are abutted, face-to-face, and are positioned longitudinally toward the male coupling-half 210 (in comparison to the circumferential interface 250). It can be said that, while in the operably coupled configuration, the male coupling shuttle valve member 230 and the female coupling shuttle valve member 280 are longitudinally biased towards the male coupling-half 210 because their abutting faces are positioned longitudinally away from the circumferential interface 250 towards the side of the male coupling-half 210.

The fluid flow through coupling 200 can be in the direction from the first connection 212 to the second connection 262, or vice versa. The coupling 200 is not limited to having the fluid flow therethrough in one particular direction. Rather, fluid can flow through coupling 200 in either direction.

The flow path 299 from the first connection 212 to the second connection 262 (i.e., from bottom to top in FIGS. 23 and 25) passes through the coupling 200 as follows. Fluid enters the first connection 212 and passes into a first male coupling-half internal space 216 defined by the male coupling-half 210. The flow path 299 then enters into an internal male coupling shuttle valve member space 232 defined by the male coupling shuttle valve member 230. The flow path 299 then passes through one or more male coupling shuttle valve apertures 234 defined by the male coupling shuttle valve member 230 and into a second male coupling-half internal space 218 defined by the male coupling-half 210. The flow path 299 then passes through one or more female coupling shuttle valve apertures 284 defined by the female coupling shuttle valve member 280 and into an internal female coupling shuttle valve member space 282 defined by the female coupling shuttle valve member 280. The flow path 299 then enters a female coupling-half internal space 286 defined by the female coupling-half 280, and then passes out through the second connection 262.

The flow path 299 from the second connection 262 to the first connection 212 (i.e., from top to bottom in FIGS. 23 and 25) passes through the coupling 200 as follows. Fluid enters the second connection 262 and passes into the female coupling-half internal space 286 defined by the female coupling-half 260. The flow path 299 then enters into the internal female coupling shuttle valve member space 282 defined by the female coupling shuttle valve member 280. The flow path 299 then passes through one or more female coupling shuttle valve apertures 284 defined by the female coupling shuttle valve member 280 and into the second male coupling-half internal space 218 defined by the male coupling-half 210. The flow path 299 then passes through one or more male coupling shuttle valve apertures 234 defined by the male coupling shuttle valve member 230 and into the internal male coupling shuttle valve member space 232 defined by the male coupling shuttle valve member 230. The flow path 299 then enters the first male coupling-half internal space 216 defined by the male coupling-half 210, and then passes out through the first connection 212.

In some embodiments, the first connection 212 and/or the second connection 262 are formed integrally with the other portions of the male coupling-half 210 and/or the female coupling-half 260. Alternatively, in some embodiments the first connection 212 and/or the second connection 262 are formed separately from other portions of the male coupling-half 210 and/or the female coupling-half 260, and then subsequently affixed to the other portions of the male coupling-half 210 and/or the female coupling-half 260 respectively. Such a manufacturing technique can be referred to as modular construction. Joining techniques such as, but not limited to, ultrasonic welding, laser welding, solvent bonding, gluing, overmolding, insert molding, and the like, and combinations thereof, can be used to affix the first connection 212 and/or the second connection 262 with the other portions of the male coupling-half 210 and/or the female coupling-half 260.

Figure 30:
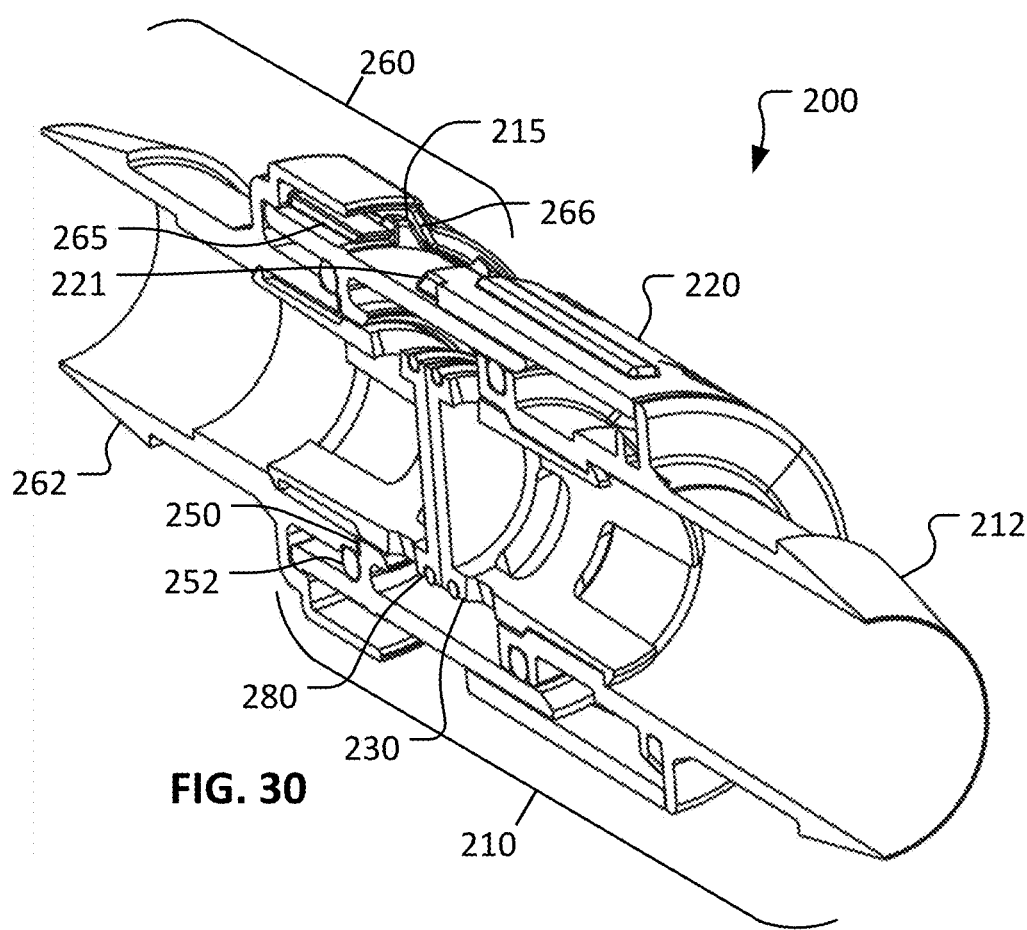
FIG. 30 is a perspective view of a longitudinal cross-sectional view of the fluid coupling device of FIG. 22.

Referring also to FIG. 30 (with locking collar 222 not shown), while the fluid coupling 200 is in its operably coupled configuration as shown, the coupling halves 210 and 260 cannot be rotated in relation to each other. That is the case because a projection 215 that is affixed to the male coupling-half 210 is rotationally captured between a latch member 265 and a wall 266 that are both attached to the female coupling-half 260. Accordingly, as described further below, the coupling halves 210 and 260 cannot be rotated in relation to each other until the locking sleeve 220 has been slid (translated longitudinally) to a position near to the female coupling-half 260. Then, while the locking sleeve 220 is at its end of travel position near to the female coupling-half 260, the latch member 265 will be actuated so that the projection 215 will no longer be detained by the latch member 265. In that arrangement, as described further below, the user can rotate the coupling halves 210 and 260 in relation to each other to disengage the bayonet connection. Conversely, until the locking sleeve 220 is slid (translated longitudinally) to its end of travel position near to the female coupling-half 260, the coupling halves 210 and 260 cannot be rotated in relation to each other. Instead, the coupling halves 210 and 260 remain locked in the operably coupled configuration.

Still referring to FIGS. 22-25, in the operably coupled configuration as shown, the locking sleeve 220 is detained in its longitudinal position on the male coupling-half 210 by the locking collar 222. As described above, the locking collar 222 must be removed in order to allow the locking sleeve 220 to be slid from its orientation in the operably coupled configuration to a position near to the female coupling-half 260. Unless the locking collar 222 is removed from between the locking sleeve 220 and the female coupling-half 260, the locking sleeve 220 cannot be slid towards the female coupling-half 260.

It should be understood from the foregoing description that, while the coupling 200 is in the operably coupled configuration, no reconfiguration of the coupling 200 is likely to occur unintentionally. That is the case, for example, because the coupling halves 210 and 260 cannot be rotated in relation to each other, and because the locking sleeve 220 cannot be slid from its orientation in the operably coupled configuration unless the locking collar 222 is removed from between the locking sleeve 220 and the female coupling-half 260. Hence, without intentional actions of a user, the coupling 200 will steadfastly remain in its operably coupled configuration.

The arrangement and operation of the coupling 200 in its operably coupled configuration has now been described. The following figures and description will provide step-by-step details of techniques for disconnecting the male coupling-half 210 from the female coupling-half 260. It should be understood from the following figures and description that the structure of the coupling 200 ensures that the coupling 200 provides a single-use, aseptic disconnection fluid coupling device that substantially prevents fluid discharge when being disconnected.

Referring to FIGS. 26-29, for the depicted embodiment of coupling 200, the technique for disconnection of the male coupling-half 210 from the female coupling-half 260 begins with removing the locking collar 222 and then sliding the locking sleeve 220 towards the female coupling-half 260. These figures show the position of the locking sleeve 220 after the locking sleeve 220 has been slid fully towards the female coupling-half 260.

In the depicted embodiment, the locking sleeve 220 cannot be slid longitudinally towards the female coupling-half 260 until the locking collar 222 has been physically removed from the rest of the coupling 200. In some embodiments, other types of mechanisms are used for locking/unlocking the locking sleeve 220.

As the locking sleeve 220 is translated toward the female coupling-half 260, an inner male coupling-half barrel member 211 slides within an outer male coupling-half barrel member 213 that remains stationary. The inner male coupling-half barrel member 211 is coupled with the locking sleeve 220. Consequently, the inner male coupling-half barrel member 211 moves in conjunction with the locking sleeve 220. The outer male coupling-half barrel member 213 remains stationary in relation to the female coupling-half 260 while the locking sleeve 220 and the inner male coupling-half barrel member 211 are translated longitudinally toward the female coupling-half 260. An o-ring seal 215 is disposed between the inner male coupling-half barrel member 211 and the outer male coupling-half barrel member 213 to provide a fluid seal therebetween.

As the locking sleeve 220 and the inner male coupling-half barrel member 211 are translated longitudinally toward the female coupling-half 260, the male coupling shuttle valve member 230 also translates longitudinally towards the female coupling-half 260. That is the case because the male coupling shuttle valve member 230 is coupled to the inner male coupling-half barrel member 211. Moreover, because the male coupling shuttle valve member 230 is abutted face-to-face with the female coupling shuttle valve member 280, the female coupling shuttle valve member 280 is also forced to translate longitudinally towards the female coupling-half 260.

The locking sleeve 220 can be manually translated longitudinally towards the female coupling-half 260 until the position of the face-to-face abutment of the male coupling shuttle valve member 230 and the female coupling shuttle valve member 280 is longitudinally aligned with the circumferential interface 250 between the coupling halves 210 and 260. This is the arrangement shown in FIGS. 26-29. When the shuttle valve members 230 and 280 reach the arrangement shown in FIGS. 26-29, both of the shuttle valve members 230 and 280 become detained in those respective positions (where the face-to-face abutment of the shuttle valve members 230 and 280 is longitudinally aligned with the circumferential interface 250).

Figure 23:
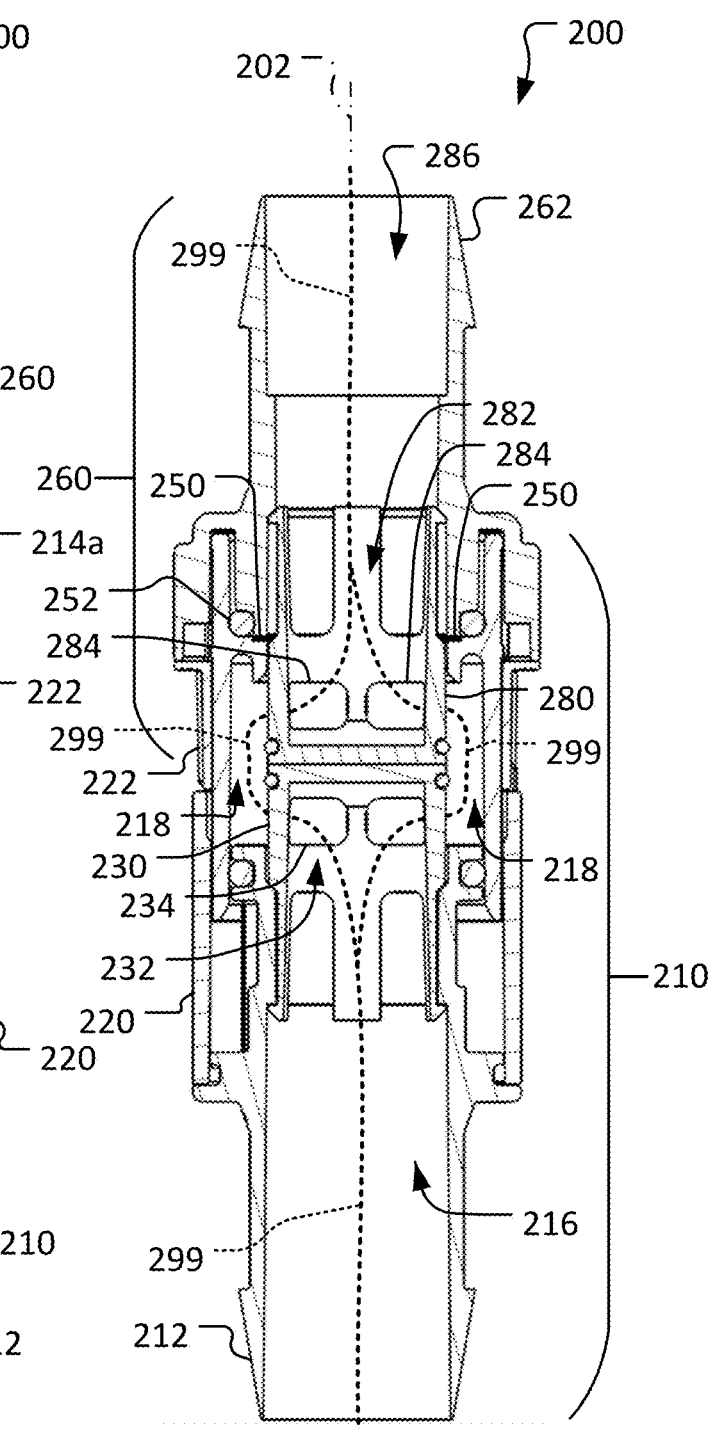
FIG. 23 is a longitudinal cross-sectional view of the fluid coupling device of FIG. 22.
Figure 24:
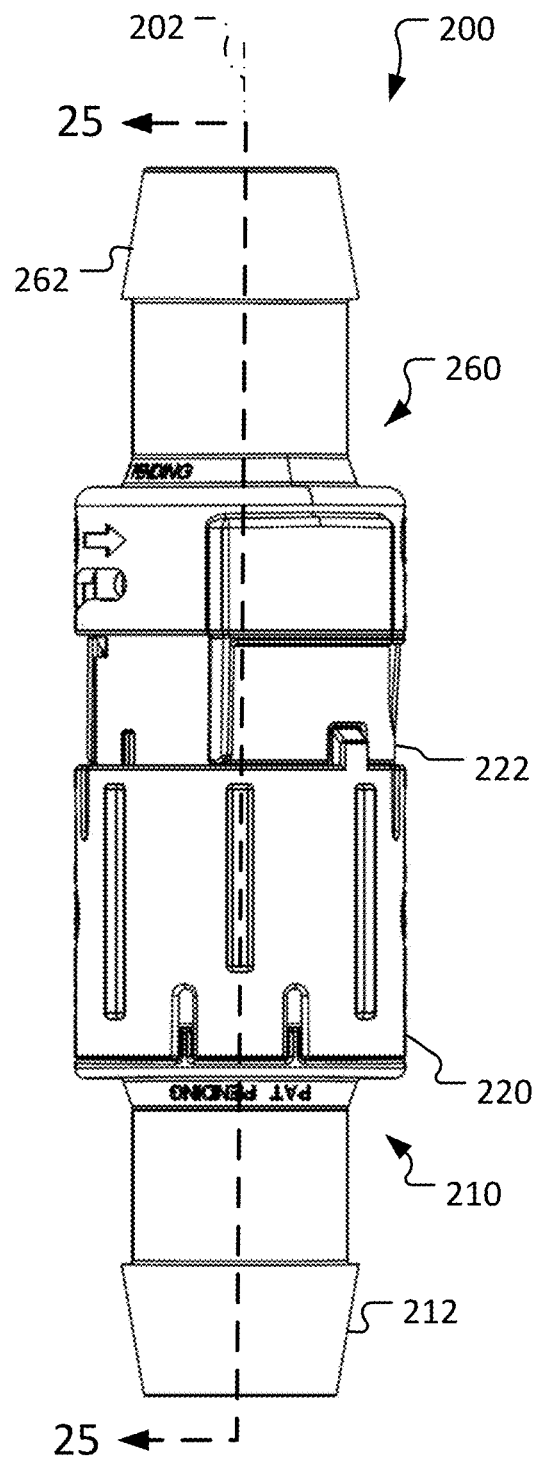
FIG. 24 is a second side view of the fluid coupling device of FIG. 22. The perspective of the second side view of FIG. 24 is about 90° from the first side view of FIG. 22.
Figure 25:
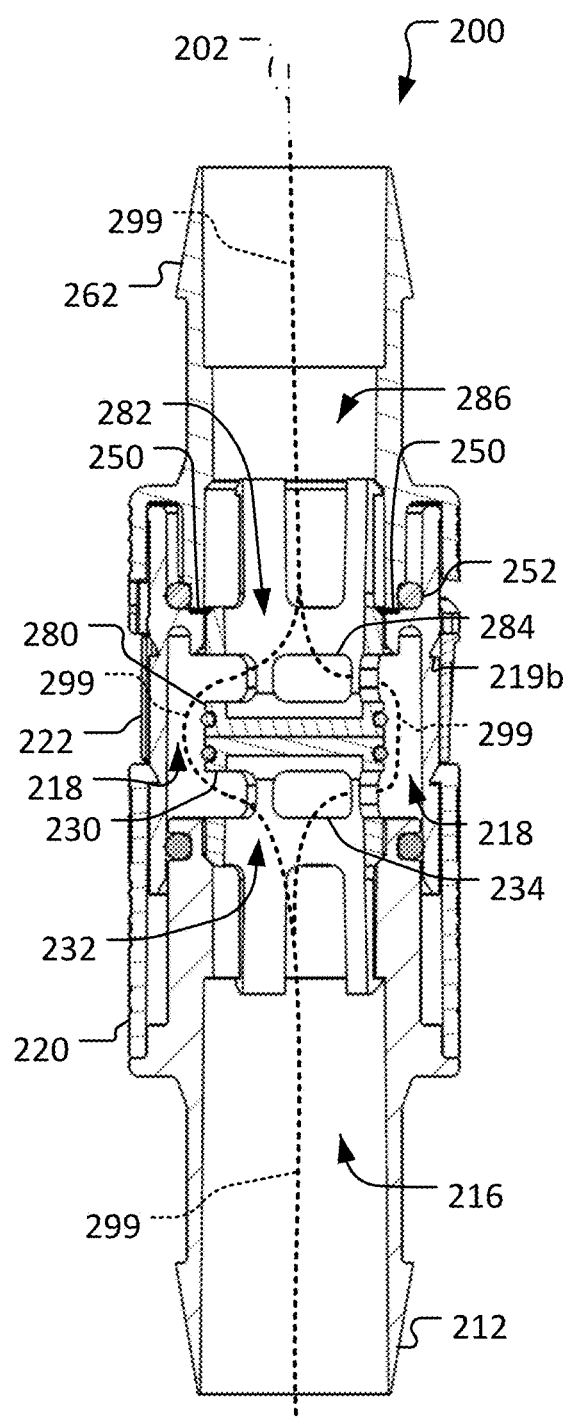
FIG. 25 is a longitudinal cross-sectional view of the fluid coupling device of FIG. 24.
Figure 26:
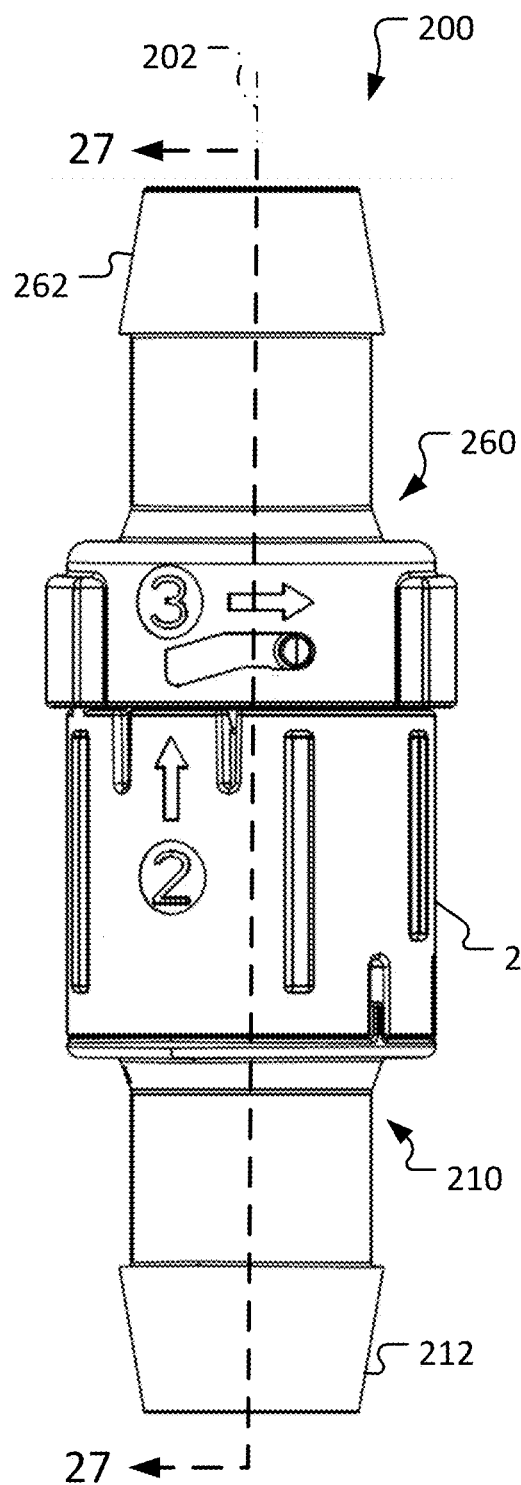
FIG. 26 is a first side view of the fluid coupling device of FIG. 22 with the coupling halves of the coupling device positioned in a longitudinally compressed arrangement (e.g., during a process of disconnecting the coupling halves from each other).
Figure 27:
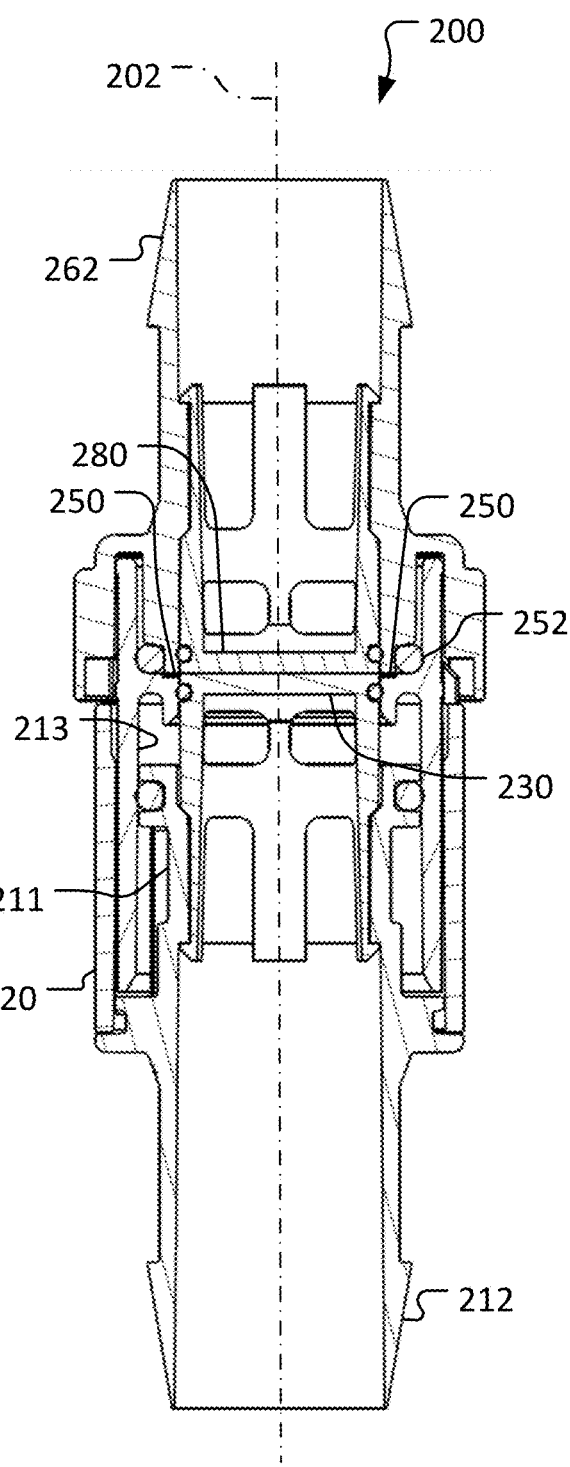
FIG. 27 is a longitudinal cross-sectional view of the fluid coupling device of FIG. 26.

The arrangement shown in FIGS. 26-29 results in a blockage of the previously existing flow path 299 (refer to FIGS. 23 and 25). That is, when the locking sleeve 220 is slid longitudinally to its end-of-travel position near to the female coupling-half 260 (as shown in FIGS. 26-29), a flow path no longer exists between the first connection 212 and the second connection 262. Rather, the longitudinal sliding of the locking sleeve 220 to its end-of-travel position near to the female coupling-half 260 (as shown in FIGS. 26-29) eliminates the previously existing flow path 299 between the first connection 212 and the second connection 262. What is more, because both of the shuttle valve members 230 and 280 become detained in their respective positions (as shown in FIGS. 26-29), the previously existing flow path 299 cannot be reestablished after the locking sleeve 220 is slid longitudinally to its end-of-travel position near to the female coupling-half 260. Rather, the flow path 299 through coupling 200 is permanently blocked. Hence, coupling 200 is referred to as a single-use coupling.

In some embodiments, the locking sleeve 220 is configured to be detained in its end-of-travel positions. For example, in the depicted embodiment the locking sleeve 220 includes one or more inward projection(s) 223 that can mate with either of a first recess 219a or a second recess 219b (or multiples thereof) that are defined by the outer male coupling-half barrel member 213. Prior to sliding the locking sleeve 220 to its end-of-travel position near to the female coupling-half 260, the inward projection(s) 223 can be releasably engaged with the first recess 219a. Then, while the locking sleeve 220 is at its end-of-travel position near to the female coupling-half 260, the inward projection(s) 223 can be un-releasably engaged with the second recess 219b (see also FIG. 25).

The inward projection(s) 223 and the complementary second recess 219b can be configured to latch-ably detain the locking sleeve 220 in its end-of-travel position near to the female coupling-half 260. For example, in the depicted embodiment the inward projection(s) 223 and the complementary second recess 219b are ramped or beveled on the leading end but not on the trailing end. Hence, when the inward projection(s) 223 engages with the complementary second recess 219b, the locking sleeve 220 will be latched and un-releasably detained in its end-of-travel position near to the female coupling-half 260.

In the depicted embodiment, the coupling halves 210 and 260 cannot be rotated in relation to each other unless the shuttle valve members 230 and 280 are each longitudinally located in their fully closed position. It follows that the coupling halves 210 and 260 cannot be disconnected from each other unless the shuttle valve members 230 and 280 are each in their fully closed position. One of skill in the art will recognize that this structure prevents biological contamination of the fluid flow paths of the coupling halves 210 and 260 because the coupling halves 210 and 260 can only be disconnected from each other if the shuttle valve members 230 and 280 are each in their fully closed position. In addition, as described further below, when the shuttle valve members 230 and 280 are in their fully closed position, the shuttle valve members 230 and 280 are locked (detained) therein. Hence, coupling 200 is referred to herein as a single-use, aseptic disconnect coupling.

As described above, prior to sliding the locking sleeve 220 to configure the coupling 200 in the arrangement shown in FIGS. 26-29, the coupling halves 210 and 260 could not be rotated in relation to each other. However, with the locking sleeve 220 at its end of travel position near to the female coupling-half 260, relative rotation between the coupling halves 210 and 260 is no longer structurally prevented.

Figure 31:
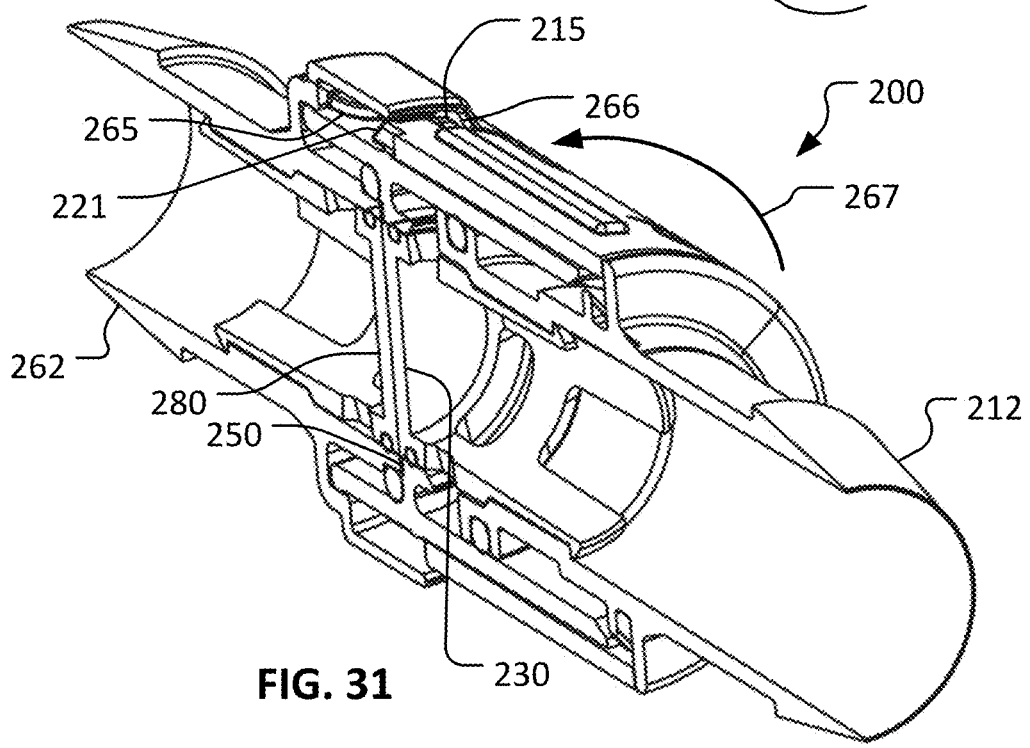
FIG. 31 is a perspective view of a longitudinal cross-sectional view of the fluid coupling device of FIG. 26.

Referring also to FIG. 31, relative rotation between the coupling halves 210 and 260 is no longer structurally prevented when the locking sleeve 220 is at its end of travel position near to the female coupling-half 260. That is the case because the latch member 265 becomes actuated by virtue of positioning the locking sleeve 220 at its end of travel position near to the female coupling-half 260. More particularly, locking sleeve 220 includes a latch actuation member 221 that makes contact with the latch member 265 when the locking sleeve 220 is at its end of travel position near to the female coupling-half 260. For example, in the depicted embodiment the latch actuation member 221 includes a beveled leading end that deflects the latch member 265 out of the way of the projection 215. Then, the latch member 265 no longer restrains the projection 215 from rotational movement. Rotation of the male coupling-half 210 in relation to the female coupling-half 260 can take place by rotating the projection 215 away from the wall 266 as depicted by an arrow 267.

Figure 32:
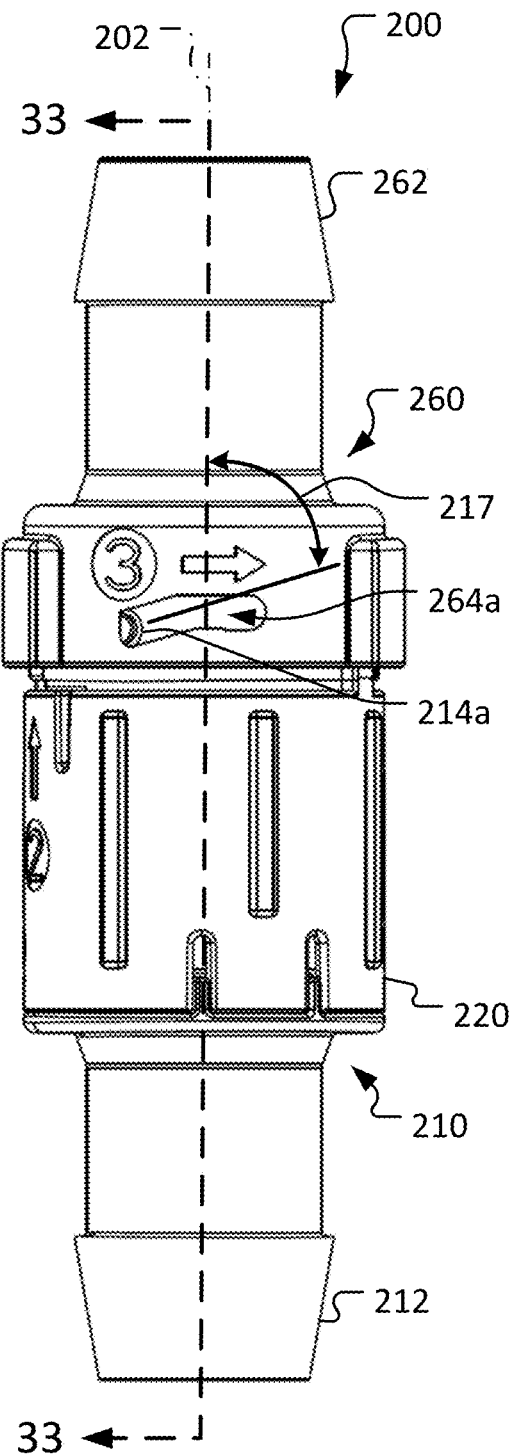
FIG. 32 is a side view of the fluid coupling device of FIG. 22 with the coupling halves of the coupling device positioned in a longitudinally compressed and rotated arrangement (e.g., during the process of disconnecting the coupling halves from each other).
Figure 33:
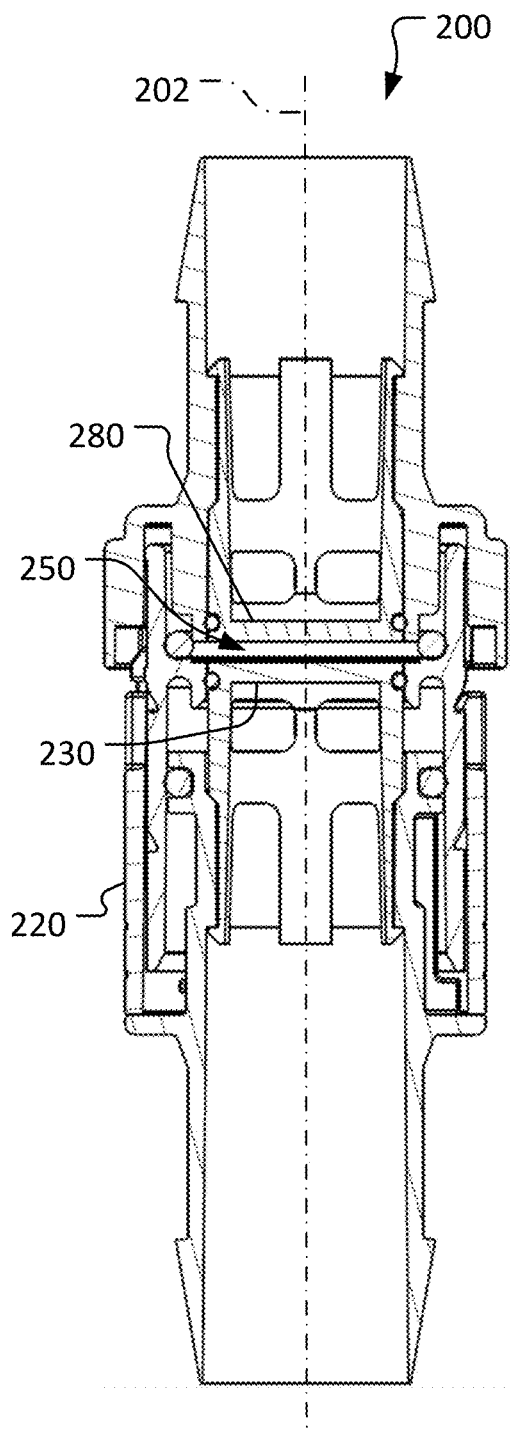
FIG. 33 is a longitudinal cross-sectional view of the fluid coupling device of FIG. 32.

Referring to FIGS. 32 and 33, the next step in the process for disconnecting the coupling halves 210 and 260 from each other is rotation of the coupling halves 210 and 260 in relation to each other. Such a rotation will partly disengage the bayonet connection mechanism between the coupling halves 210 and 260. FIGS. 32 and 33 show the coupling halves 210 and 260 after the rotation has been completed.

As the coupling halves 210 and 260 are rotated in relation to each other, the two radially protruding posts 214a and 214b slide within the two corresponding slots 264a and 264b. In some embodiments, such as the depicted embodiment, the slots 264a and 264b are not totally orthogonal with the longitudinal axis 202. Rather, in the depicted embodiment a portion of the slots 264a and 264b extends at a non-orthogonal angle 217 in relation to the longitudinal axis 202. In some embodiments, the non-orthogonal angle 217 is in a range from about 85° to about 90°, or about 80° to about 90°, or about 75° to about 85°, or about 70° to about 80°, or about 60° to about 70°, or about 50° to about 60°. In some embodiments, the slots 264a and 264b are generally orthogonal to the longitudinal axis 202.

Because the slots 264a and 264b of the depicted embodiment extend along the non-orthogonal angle 217, as the coupling halves 210 and 260 are rotated in relation to each other the coupling halves 210 and 260 will also translate longitudinally in relation to each other. That is, as the two radially protruding posts 214a and 214b are slid within the two corresponding slots 264a and 264b along the non-orthogonal angle 217 by the relative twisting of the coupling halves 210 and 260, the two radially protruding posts 214a and 214b travel longitudinally and cause the male coupling-half 210 to also travel longitudinally (in relation to the female coupling-half 260). Hence, the coupling halves 210 and 260 become slightly longitudinally separated from each other as the coupling halves 210 and 260 are rotated in relation to each other. This separation is visible in FIG. 33 at the circumferential interface 250. A gap exists there between the male coupling-half 210 and the female coupling-half 260 where the two previously directly abutted each other.

The structures that result in the coupling halves 210 and 260 becoming slightly separated from each other as the coupling halves 210 and 260 are rotated in relation to each other can be advantageous in some cases. For example, the resulting slight separation may be advantageous for breaking a seal (or vacuum) that may exist between the coupling halves 210 and 260, and that may otherwise be difficult or inconvenient for a user to break.

As described above, each slot 264a and 264b has an end-of-slot-aperture through which the radially protruding posts 214a and 214b can pass, respectively. In the arrangement of FIGS. 32 and 33, the radially protruding posts 214a and 214b are longitudinally aligned with the end-of-slot-apertures of slots 264a and 264b respectively.

Referring to FIGS. 34 and 35, the coupling halves 210 and 260 of coupling 200 can be disconnected (uncoupled) from each other. With the radially protruding posts 214a and 214b longitudinally aligned with the end-of-slot-apertures of slots 264a and 264b respectively, the male coupling-half 210 can be separated from the female coupling-half 260 by simply pulling them apart longitudinally.

FIG. 35 illustrates that, when the coupling halves 210 and 260 are disconnected from each other, the face of the male coupling shuttle valve member 230 is substantially flush with the end of the male coupling bore 224. Similarly, the face of the female coupling shuttle valve member 280 is substantially flush with the end of the female coupling bore 288. In addition, FIG. 35 illustrates that an o-ring 231 is positioned between the male coupling shuttle valve member 230 and the male coupling bore 224, near to the end of the male coupling bore 224. Similarly, an o-ring 281 is positioned between the female coupling shuttle valve member 280 and the female coupling bore 288, near to the end of the female coupling bore 288.

The arrangement where the face of the male coupling shuttle valve member 230 is substantially flush with the end of the male coupling bore 224, and the o-ring 231 is near to the end of the male coupling bore 224, inhibits or substantially prevents biological contamination from entering the male coupling-half 210. Similarly, the arrangement where the face of the female coupling shuttle valve member 280 is substantially flush with the end of the female coupling bore 288, and the o-ring 281 is near to the end of the female coupling bore 288, inhibits or substantially prevents biological contamination from entering the female coupling-half 260. In other words, these structural features make coupling 200 an aseptic disconnection fluid coupling device.

In addition, the aforementioned arrangement regarding the faces of the coupling shuttle valve members 230 and 280 being substantially flush with the ends of the coupling bores 224 and 288, and the o-rings 231 and 281 being near to the ends of the coupling bores 224 and 288 substantially prevents fluid discharge when the coupling halves 200 and 260 are being disconnected from each other.

When the coupling halves 210 and 260 have been disconnected from each other using the process described above, particular components of the coupling 200 are detained (effectively locked) in their respective positions. For example, the shuttle valve members 230 and 280 are detained in relation to the coupling bores 224 and 288. In addition, the locking sleeve 220 is detained in its position longitudinally on the male coupling-half 210. Hence, even if the bayonet connection between the coupling halves 210 and 260 is restored, the flow path through coupling 200 will not be reopened. For this reason, the coupling 200 is termed as a single-use coupling device. In other words, once the coupling halves 210 and 260 have been disconnected from each other, the coupling halves 210 and 260 cannot be reconnected so as to recreate a flow path through the coupling 200.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A fluid coupling device comprising:
   a male coupling component including a male coupling shuttle valve member that is slidable along a longitudinal axis of the male coupling component; and
   a female coupling component including a female coupling shuttle valve member that is slidable along a longitudinal axis of the female coupling component,
   wherein the male and female coupling components are coupleable in a first arrangement in which an open flow path exists through each of the male and female coupling components and in a second arrangement in which: (i) the male coupling shuttle valve member is permanently locked in an end-of-travel position in which the male coupling shuttle valve member blocks flow through the male coupling component and (ii) the female coupling shuttle valve member is permanently locked in an end-of-travel position in which the female coupling shuttle valve member blocks flow through the female coupling component,
   wherein the male and female coupling components are only disconnectable from each other while in the second arrangement.

2. The fluid coupling device of claim 1, wherein while the male coupling shuttle valve member is locked in its end-of-travel position a face of the male coupling shuttle valve member is flush with an end of a bore defined by the male coupling component, and wherein while the female coupling shuttle valve member is locked in its end-of-travel position a face of the female coupling shuttle valve member is flush with an end of a bore defined by the female coupling component.

3. The fluid coupling device of claim 2, further comprising:
   a first seal member positioned between the male coupling shuttle valve member and the bore defined by the male coupling component; and
   a second seal member positioned between the female coupling shuttle valve member and the bore defined by the female coupling component.

4. The fluid coupling device of claim 1, wherein the male and female coupling components are rotatable relative to each other while in the second arrangement between an engaged arrangement and a partly disengaged arrangement.

5. The fluid coupling device of claim 4, wherein the male and female coupling components can be separated from each other while in the partly disengaged arrangement by translating them longitudinally apart from each other.

6. The fluid coupling device of claim 4, wherein the male and female coupling components are caused to translate relative to each other as the male and female coupling components are rotated relative to each other between the engaged arrangement and the partly disengaged arrangement.

7. The fluid coupling device of claim 1, further comprising a locking sleeve movably coupled to the male coupling component, and wherein while the male and female coupling components are coupled in the first arrangement, the locking sleeve is operably coupled with the male coupling shuttle valve member such that a movement of the locking sleeve causes a corresponding movement of the male coupling shuttle valve member.

8. The fluid coupling device of claim 7, wherein the locking sleeve is slidably coupled to the male coupling component.

9. The fluid coupling device of claim 1, wherein cross-sectional shapes of the male coupling shuttle valve member and the female coupling shuttle valve member are each circular.

10. The fluid coupling device of claim 1, wherein the male coupling shuttle valve member and the female coupling shuttle valve member each include one or more apertures through which the open flow path exists.

11. The fluid coupling device of claim 1, further comprising a removable locking collar releasably coupleable with the fluid coupling device while the male and female coupling components are coupled in the first arrangement.

12. The fluid coupling device of claim 11, wherein the removable locking collar prevents reconfiguring of the male and female coupling components from the first arrangement to the second arrangement while the removable locking collar is coupled with the fluid coupling device.

* * * * *